US011103520B2

(12) United States Patent
Demetriou et al.

(10) Patent No.: US 11,103,520 B2
(45) Date of Patent: Aug. 31, 2021

(54) ANALOGS OF N-ACETLYGLUCOSAMINE AND USES THEREOF

(71) Applicants: THE REGENTS OF THE UNIVERSITY OF CALIFORNIA, Oakland, CA (US); James Dennis, Ontario (CA)

(72) Inventors: Michael Demetriou, Irvine, CA (US); James Dennis, Ontario (CA); Ani Oganesyan, Santa Rosa, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 51 days.

(21) Appl. No.: 15/305,609

(22) PCT Filed: Apr. 23, 2015

(86) PCT No.: PCT/US2015/027325
§ 371 (c)(1),
(2) Date: Oct. 20, 2016

(87) PCT Pub. No.: WO2015/164622
PCT Pub. Date: Oct. 29, 2015

(65) Prior Publication Data
US 2017/0042919 A1 Feb. 16, 2017

Related U.S. Application Data

(60) Provisional application No. 61/983,182, filed on Apr. 23, 2014.

(51) Int. Cl.
*A61K 31/7008* (2006.01)
*A61K 31/726* (2006.01)
*A61K 45/06* (2006.01)
*A23L 33/10* (2016.01)

(52) U.S. Cl.
CPC .......... *A61K 31/7008* (2013.01); *A23L 33/10* (2016.08); *A61K 31/726* (2013.01); *A61K 45/06* (2013.01)

(58) Field of Classification Search
CPC .. A61K 31/7008; A61K 31/726; A61K 45/06; A23L 33/10
See application file for complete search history.

(56) References Cited

U.S. PATENT DOCUMENTS

| | | | | |
|---|---|---|---|---|
| 2001/0002396 A1* | 5/2001 | Achkar | ..................... | A61K 8/67 514/167 |
| 2006/0020127 A1* | 1/2006 | Miura | ...................... | A61K 8/60 536/53 |
| 2006/0216361 A1* | 9/2006 | Edwards | .............. | A61K 31/525 424/682 |
| 2007/0082851 A1* | 4/2007 | Ichikawa | ............... | A61K 31/13 514/25 |
| 2009/0099130 A1 | 4/2009 | Demetriou et al. | | |

FOREIGN PATENT DOCUMENTS

WO   WO-2009020641 A1 *  2/2009  ......... A61K 31/7008

OTHER PUBLICATIONS

Grigorian et al., (JBC. Nov. 18, 2011;286(46:)40133-40141). (Year: 2011).*
Coburn et al., "Short-Chain Fatty Acid-Modified Hexosamine for Tissue-Engineering Osteoarthritic Cartilage," Tissue Engineering: Part A, vol. 19, Nos. 17 and 18 (2013).*
Kwok et al., "Retinoic acid attenuates rheumatoid inflammation in mice," J Immunol. Jul. 15, 2012;189(2), 1062-1071.*
Azuma et al., "Suppressive Effects of N-Acetyl-D-Glucosamine on Rheumatoid Arthritis Mouse Models," Inflammation, 2012, 35(4):1462-1465.
Chen et al., "T Cell Receptor Signaling Co-regulates Mulitple Golgi Genes to Enhance N-Glycan Branching," J. Biol. Chem., 2009, 284:32454-32461.
Grigorian et al., "N-Acetylglucosamine Inhibits T-helper (Th1)/T-helper 17 (Th17) Cell Responses and Treats Experimental Autoimmune Encephalomyelitis," The Journal of Biological Chemistry, 2011, 286(46):40133-40141.
Lee et al., "N-Glycan Processing Deficiency Promotes Spontaneous Inflammatory Demyelination and Neurodegeneration," The Journal of Biological Chemistry, 2007, 282(46):33725-33734.
Salvatore et al., "A pilot study of N-acetyl glucosamine, a nutritional substrate for glycosaminoglycan synthesis, in paediatric chronic inflammatory bowel disease," Aliment Phrmacol Ther, 2000, 14:1567-1579.
Vaitaitis et al., "CD40 glycoforms and TNF-receptors 1 and 2 in the formation of CD40 receptor(s) in autoimmunity," Molecular Immunology, 2010, 47:2303-2313.

* cited by examiner

*Primary Examiner* — Jared Barsky
(74) *Attorney, Agent, or Firm* — Riverside Law LLP

(57) ABSTRACT

The present invention includes a novel method of treating or preventing a disease or disorder associated with low levels of branched N-glycans in a subject in need thereof, the method comprising administering to the subject an effective amount of a compound of the invention. In one embodiment, the subject is further administered at least one additional therapeutic agent.

4 Claims, 16 Drawing Sheets

ANALOGS OF N-ACETLYGLUCOSAMINE AND USES THEREOF

CROSS-REFERENCE TO RELATED APPLICATIONS

This application is the U.S. national phase application filed under 35 U.S.C. § 371 claiming benefit to International Patent Application No. PCT/US15/27325, filed Apr. 23, 2015, which is entitled to priority under 35 U.S.C. § 119(e) to U.S. Provisional Patent Application No. 61/983,182, filed Apr. 23, 2014, each of which application is hereby incorporated herein by reference in its entirety.

STATEMENT REGARDING FEDERALLY SPONSORED RESEARCH OR DEVELOPMENT

This invention was made in part with U.S. Government support under Grant No. R01AI053331, awarded by the National Institutes of Health, NIAID. The U.S. Government has certain rights in this invention.

BACKGROUND OF THE INVENTION

Human autoimmunity is a complex trait that develops from intricate and poorly understood interactions between an individual's genetics and their environmental exposures. Golgi Asn (N)-linked protein glycosylation co-regulates homeostatic set points for T cell growth, differentiation, and self-tolerance to influence risk of autoimmune disorders such as multiple sclerosis (MS), type I diabetes, rheumatoid arthritis (RA), autoimmune glomerulonephritis, and systemic lupus erythematosus (SLE). MS and RA are among the most common autoimmune diseases in the northern hemisphere. RA is a long-term disease that leads to inflammation of the joints and surrounding tissues and usually requires lifelong treatment, including medications, physical therapy, and even surgery. It is estimated that at least 1.3 million U.S. adults have RA. SLE is a systemic autoimmune disease that can affect any part of the body and is characterized by multisystem micro-vascular inflammation with the generation of autoantibodies. In the U.S. approximately 250,000 people have SLE. SLE carries a highly variable prognosis for individual patients and is treated with broad immunosuppression. MS is an autoimmune disorder that affects the central nervous system and is characterized by inflammatory demyelination and neurodegeneration. MS can result in a variety of neurological dysfunctions, such as blindness, paralysis, and cognitive dysfunction. MS is the most common cause of neurological disability in young adults and has been estimated to afflict 300,000-400,000 people in the U.S.

Current MS treatment strategies are predominated by palliative injectable therapies that have modest efficacy, high cost, and/or side effects that limit tolerability and compliance. More recently developed oral agents have shown efficacy, but also significant toxicity and other adverse side effects. These oral agents broadly and nonspecifically suppress the immune system, a questionable approach given recently increased understanding of the pathogenic mechanisms underlying MS. The limitations and disadvantages of current medications highlight the need for improved pharmaceutical agents for the treatment of MS and other autoimmune diseases.

Previously published data revealed that the simple sugar and dietary supplement N-acetylglucosamine (GlcNAc) inhibits T cell function and autoimmunity by enhancing N-glycan branching in T cells.

There is a need in the art for novel methods for the treatment of diseases and disorders requiring enhancement of N-glycan branching, such as MS and RA. The present invention addresses this unmet need.

SUMMARY OF THE INVENTION

The present invention relates to a method of treating or preventing a disease or disorder associated with low levels of branched N-glycans in a subject in need thereof. The method includes the step of administering to the subject a therapeutically effective amount of a pharmaceutical composition comprising at least one compound of formula (I):

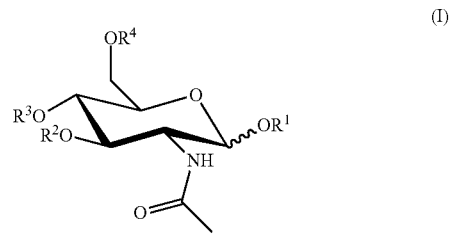

wherein:

$R^1$, $R^2$, $R^3$, and $R^4$ are each independently selected from the group consisting of H, C(O)R', $C_1$-$C_5$ alkyl, $C_2$-$C_5$ alkenyl, cycloalkyl, aryl, arylalkyl, and an unsaturated or saturated aliphatic moiety of a 6-carbon to 22-carbon medium- or a long chain fatty acid, wherein the alkyl, alkenyl, cycloalkyl, aryl, and arylalkyl group may be optionally substituted; and R' is selected from the group consisting of H, $C_1$-$C_5$ alkyl, $C_2$-$C_5$ alkenyl, cycloalkyl, aryl, arylalkyl, and an unsaturated or saturated aliphatic moiety of a 6-carbon to 21-carbon medium- or long chain fatty acid, wherein the alkyl, alkenyl, cycloalkyl, aryl, and arylalkyl group may be optionally substituted;

with the proviso that at least one of $R^1$, $R^2$, $R^3$, and $R^4$ is not H, and that $R^1$, $R^2$, $R^3$, and $R^4$ cannot simultaneously be C(O)Me; and a salt or solvate thereof, and any combination thereof.

In one embodiment, at least one of $R^1$, $R^2$, $R^3$, and $R^4$ is C(O)R'. In another embodiment, $R^4$ is C(O)R'. In another embodiment, $R^2$ is C(O)R'. In another embodiment, $R^3$ is C(O)R'. In another embodiment, one of $R^1$, $R^2$, $R^3$, and $R^4$ is C(O)R', and the rest are H. In another embodiment, $R^1$, $R^2$, and $R^3$ are each H. In another embodiment, R' is selected from the group consisting of H, methyl, propyl, butyl, isobutyl, and an unsaturated or saturated aliphatic moiety of a 6-carbon to 21-carbon medium- or long chain fatty acid. In another embodiment, R' is methyl. In another embodiment, the compound of formula (I) is selected from the group consisting of N-acetylglucosamine 3-acetate, N-acetylglucosamine 4-acetate, N-acetylglucosamine 6-acetate, N-acetylglucosamine 3,4 diacetate, N-acetylglucosamine 3,6 diacetate, N-acetylglucosamine 4,6 diacetate, and N-acetylglucosamine 3,4,6 triacetate, a salt or solvate thereof, and any combinations thereof. In another embodiment, the compound is N-acetylglucosamine 6-acetate, or a salt or solvate thereof. In another embodiment, the method further comprises administering to the subject at least one additional compound. In another embodiment, the additional compound is a compound of formula (I) that is different. In another embodiment, the additional compound is selected from the group consisting of an agonist of complex-branched N-glycans, a sugar donor for complex branched N-glycans, a metabolite of pathways for synthesis of a sugar nucleotide donor or precursors thereof, or a regulator of agonists of a sugar donor or a pathway for the synthesis of a sugar donor, and any combination thereof. In another embodiment, the at least one additional compound is a therapeutic agent. In another embodiment, the pharmaceutical composition and the at least one additional compound are co-administered to the subject. In another embodiment, the pharmaceutical composition and the at least one additional compound are co-formulated. In another embodiment, the additional compound is selected from the group consisting of an agent used for the treatment of multiple sclerosis (MS), a disease-modifying antirheumatic drug (DMARD), an immunosuppressive agent, an analgesic, an intravenous immunoglobulin (IVIG), an anti-inflammatory agent, and a neutraceutical. In another embodiment, the disease or disorder is selected from the group consisting of multiple sclerosis (MS), autoimmune diabetes, pediatric treatment-resistant inflammatory bowel disease, rheumatoid arthritis (RA), systemic lupus erythematosus (SLE), autoimmune glomerulonephritis, acute disseminated encephalomyelitis, acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome, autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura, autoimmune thyroid disease, autoimmune urticarial, an axonal & neuronal neuropathy, Balo disease, Behcet's disease, bullous pemphigoid, cardiomyopathy, Castleman disease, celiac disease, Chagas disease, chronic inflammatory demyelinating polyneuropathy, chronic recurrent multifocal osteomyelitis, Churg-Strauss syndrome, cicatricial pemphigoid/benign mucosal pemphigoid, Crohn's disease, Cogan's syndrome, cold agglutinin disease, congenital heart block, coxsackie myocarditis, CREST disease, essential mixed cryoglobulinemia, a demyelinating neuropathy, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), glomerulonephritis, Goodpasture's syndrome, granulomatosis with polyangiitis (GPA), Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, insulin-dependent diabetes (type1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), Lyme disease, chronic Meniere's disease, microscopic polyangiitis, mixed connective tissue disease, Mooren's ulcer, Mucha-Habermann disease, myasthenia gravis, myositis, narcolepsy, neuromyelitis optica (Devic's), neutropenia, ocular cicatricial pemphigoid, optic neuritis, palindromic rheumatism, pediatric autoimmune neuropsychiatric disorders associated with *Streptococcus* (PANDAS), paraneoplastic cerebellar degeneration, paroxysmal nocturnal hemoglobinuria, Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis *nodosa*, Type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reflex sympathetic dystrophy, Reiter's syndrome, relapsing polychondritis, restless legs syndrome, retroperitoneal fibrosis, rheumatic fever, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, and vitiligo. In another embodiment, the disease or disorder is selected from the group consisting of multiple sclerosis (MS), autoimmune diabetes, pediatric treatment-resistant inflammatory bowel disease, and rheumatoid arthritis (RA).

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 3A-3D, illustrates galectin binding to N-glycans. FIG. 3A is an illustration depicting that multivalent galectin (red) binds to N-glycans on surface glycoproteins (depicted as green and yellow) to form a galectin-glycoprotein lattice. FIG. 3B is a picture of a T cell slice with cell surface at top and nucleus at bottom. The galectin-glycoprotein lattice is located in the 100 nm dark band of the picture. The galectin-glycoprotein lattice regulates glycoprotein concentration, clustering, and endocytosis and thereby affects cell growth and differentiation. FIG. 3C is a diagram illustrating that galectin binding to N-glycans attached to the T cell receptor (TCR) complex prevents spontaneous TCR clustering. The peptide-major histocompatibility complex (MHC) overcomes galectin-TCR interactions to achieve TCR clustering, signaling, and growth. FIG. 3D is a diagram illustrating that galectin binding to N-glycans attached to CTLA-4 enhances surface retention by opposing endocytic loss, resulting in sustained and increased arrest signaling. Weakening the lattice enhances TCR signaling, decreases CTLA-4 growth arrest, and promotes loss of immune tolerance.

FIGS. 5A-5F, depicts matrix-assisted laser desorption/ionization-time of flight (MALDI-TOF) mass spectra and high-performance anion exchange chromatography (HPAEC)N-glycan profiles. The so-profiled N-glycans were isolated from purified $CD3^+T$ cells obtained from age and sex matched wild-type control mice or wild-type mice treated orally with GlcNAc for 7 days and analyzed by MALDI-TOF mass spectrometry (FIGS. 5A-5D) or HPAEC (FIGS. 5E and 5F). Abbreviations for individual sugars depicted in FIG. 5 are the same as those defined in FIG. 4.

FIGS. 6A-6E, illustrates experimental data demonstrating that oral GlcNAc treatment inhibits CD25 expression and pro-inflammatory cytokine production in mice. FIG. 6A is a graph that plots L-PHA Mean Fluorescence Intensity (MFI) in splenocytes isolated from mice as a function of GlcNAc treatment concentration. FIG. 6B is a series of FACS plots of CD25 and CD4 expression profiles in splenocytes from control and GlcNAc treated mice. FIG. 6C is a graph of CD25 expression levels after GlcNAc treatment as a function of MOG 35-55 peptide immunization concentrations. FIG. 6D is a graph of Foxp3 expression levels after GlcNAc treatment as a function of MOG 35-55 peptide immunization concentrations. FIG. 6E is a series of plots of IFN-γ, TNF-α, IL-17, and IL-22 expression levels in splenocytes from control and GlcNAc treated mice as a function of MOG 35-55 peptide immunization concentrations.

FIGS. 7A-7D, depicts experimental data demonstrating that oral GlcNAc treatment attenuates the clinical course of experimental autoimmune encephalomyelitis (EAE), a mouse model of multiple sclerosis, and that EAE was induced in C57BL/6 mice by immunization with MOG 35-55 peptide emulsified in Complete Freund's adjuvant and pertussis toxin. FIG. 7A is a graph that plots mean clinical EAE score as a function of days after disease onset for control and treated groups of mice. FIG. 7B is a graph that plots events as a function of (Phaseolus vulgaris leukoagglutinin) L-PHA binding, and shows that GlcNAc treatment increased N-glycan branching in T cells as seen by L-PHA staining in representative mice taken at the peak of disease. FIG. 7C is a series of FACS plots that indicate a significant reduction in $CD25^+T$ cells was observed in representative GlcNAc-treated mice taken at the peak of disease compared with control mice. FIG. 7D is a series of graphs illustrating experimental data demonstrating that plot IFN-γ, TNF-α, IL-17, or IL-22 concentration in $CD3^+T$ cells isolated from control or GlcNAc treated mice as a function of MOG 35-55 immunization concentration. p values in FIG. 7D were determined by t test. *, $p<0.05$; , $p<0.01$; *, $p<0.001$. Error bars in FIGS. 7A and 7D represent the means±S.E. of duplicate or greater values unless otherwise stated.

FIGS. 8A-8C, illustrates that oral GlcNAc treatment after disease onset attenuates the clinical course of EAE in moderate-severe disease, but not disease with rapid lethal progression. FIG. 8A is a graph that plots mean clinical EAE score for control or GlcNAc treated mice as a function of days after disease onset for moderate-severe disease. FIG. 8B is a graph that plots mean clinical EAE score for control or GlcNAc treated mice as a function of days after disease onset for lethal disease. FIG. 8C is a graph that plots L-PHA MFI in splenocytes of control and GlcNAc treated mice. p values in FIG. 8C were determined by t test. Error bars in FIG. 8C represent the means±S.E. of triplicate or greater values unless otherwise stated.

FIGS. 11A-11B, illustrates experimental data demonstrating that in human T cells N-acetylglucosamine 6-acetate inhibits CD25 and CD69 expression to greater effect than GlcNAc. FIG. 12A is a graph that plots CD25 expression (%) in human T cells as a function of α-CD3 and GlcNAc/GlcNAc 6-acetate concentrations. FIG. 12B is a graph that plots CD69 expression (%) in human T cells as a function of α-CD3 and GlcNAc/GlcNAc 6-acetate concentrations.

FIGS. 12A-12B, illustrates experimental data from human CD4$^+$T cells treated with GlcNAc and GlcNAc 6-acetate. FIG. 12A is a graph illustrating the percent proliferation of human CD4$^+$T cells. FIG. 12B is a graph illustrating T cell proliferation. Human CD4$^+$T cells were stimulated with anti-CD3 (10 μg/ml) and anti-CD28 (5 μg/ml) and treated as indicated for 5 days. T cell proliferation was measured by CFSE dilution. CD4$^+$T cells were labeled with 1 μM of CFSE prior to in vitro activation for 5 days. Overlaying histograms are gated on live, CD4$^+$ cells by FACS.

FIGS. 13A-13B, illustrates experimental data from human CD4$^+$T cells treated with GlcNAc and GlcNAc 6-acetate. FIG. 13A is a series of graphs illustrating data from cells harvested at 4 days. FIG. 13B is a series of graphs illustrating data from cells harvested at 6 days. Cells were harvested at days 4 and 6 and analyzed for surface CTLA-4 expression (MFI) by FACS. p values were determined by one-way ANOVA-Bonferroni's multiple comparison test. *, $p<0.05$; , $p<0.01$; *, $p<0.001$. Error bars represent the means±S.E.

FIG. 15, comprising FIG. 15A is a graph illustrating splenocytes from C57/BL6 female (n=6, 8-24 weeks old) or male (n=5, 10-13 weeks old) mice after culturing in the presence of anti-CD3 (1 μg/mL). Cells were collected on day 3, and labeled for FACS analysis. FIG. 15B is a series of graphs illustrating in vitro cultures of splenocytes either un-stimulated (resting) or anti-CD3 (1 μg/mL) activated. G-6-A (20 mM) and or GlcNAc (40 mM). Cells were harvested over a three-day time course, and labeled for FACS analysis. FIG. 15C is a graph illustrating in vitro stimulated splenocytes (anti-CD3 at 1 μg/mL) that were cultured for three-days and labeled for FACS analysis of the T cell activation marker CD69 at the time points indicated. FIG. 15D is a graph of experimental data demonstrating T cell proliferation as measured by CFSE dilution. Splenocytes were labeled with 1 uM of CFSE prior to in vitro anti-CD3 (1 μg/mL) activation for three-days. Overlaying histograms is on gated CD4+ cells. FIG. 15E is a graph illustrating that oral treatment with G-6-A increases N-glycan branching in mouse T cells in vivo.

DETAILED DESCRIPTION OF THE INVENTION

Figure 1:
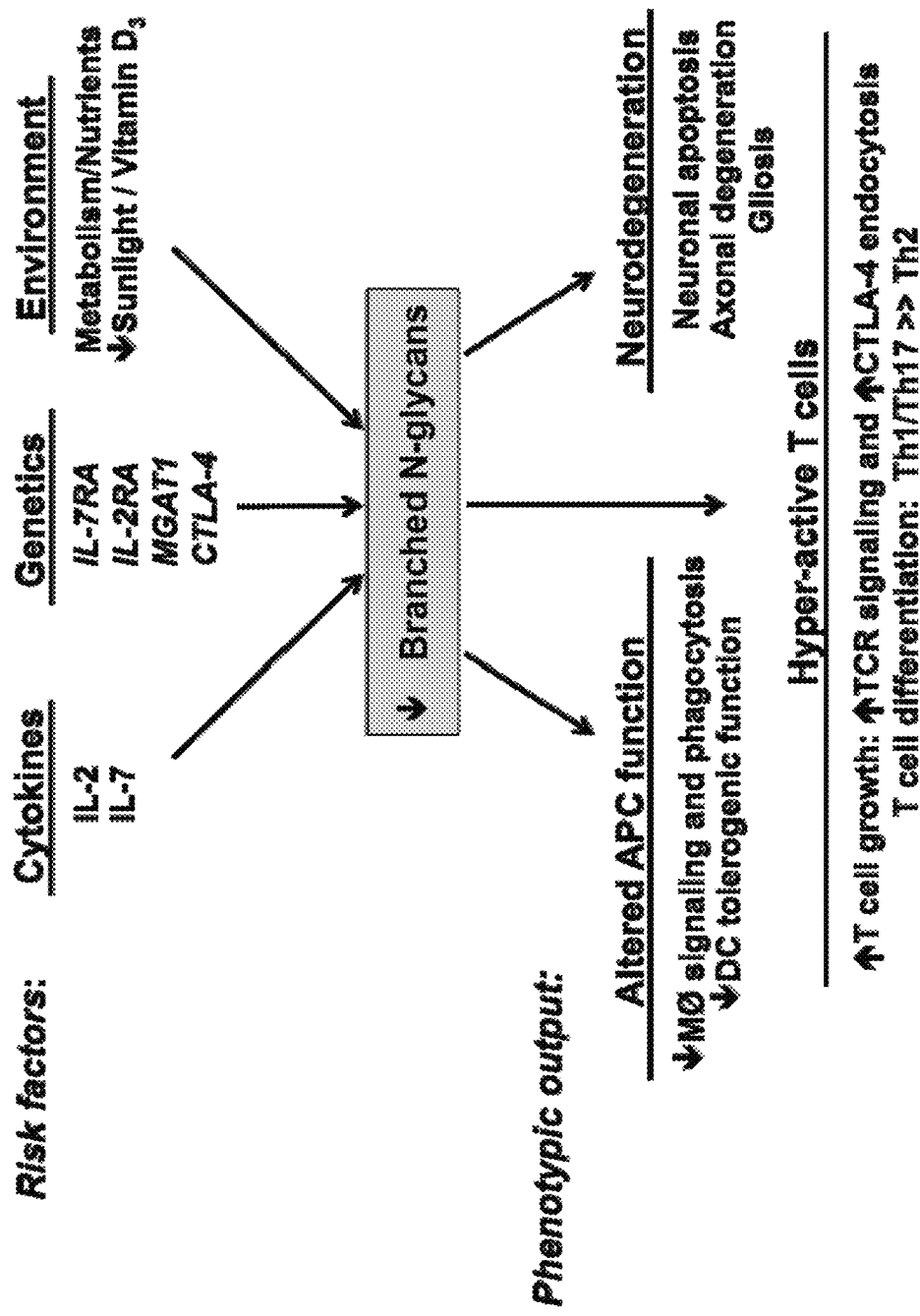
FIG. 1 is a diagram illustrating how multiple genetic risk factors for MS (IL-7RA, IL-2RA, MGAT1, and CTLA-4) combine with environmental risk factors (sunlight, metabolism, vitamin $D_3$) and with cytokines IL-2 and IL-7 to decrease N-glycan branching, which in turn promotes diverse pathogenic mechanisms of MS. Such pathogenic mechanisms promoted by decreased N-glycan levels in MS include alterations in antigen presenting cell function (APC), neurodegeneration, and T cell hyperactivity. The IL2RA*T and IL7RA*C MS risk alleles antagonize IL-2 and IL-7 signaling, leading to downregulation of Mgat1, decreased branching and CTLA-4 surface levels and increased MS risk. The MGAT1 IVAVT-T haplotype increases Mgat1, which decreases branching, CTLA-4 surface levels and increases MS risk conditional on metabolic production of UDP-GlcNAc. Combining genetic upregulation of Mgat1 by the MGAT1 IVAVT-T haplotype with genetic downregulation of Mgat1 by the IL2RA*T and IL7RA*C MS risk alleles optimizes Mgat1 activity, thereby enhancing branching, CTLA-4 surface expression and mitigating MS risk. The CTLA-4 Thr17Ala variant modifies these interactions by controlling the number of N-glycans attached to CTLA-4, with the Thr17 allele doubling N-glycan number to promote CTLA-4 surface retention and reduce MS risk when combined with MGAT1 IVAVT-T, IL2RA*TT and IL7RA*CC.

The present invention relates in part to the unexpected discovery of novel compounds that increase the amount of branched N-glycans in a subject. In one aspect, the compounds of the invention may be used to treat or prevent a disease or disorder associated with low levels of branched N-glycans in a subject in need thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated, or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

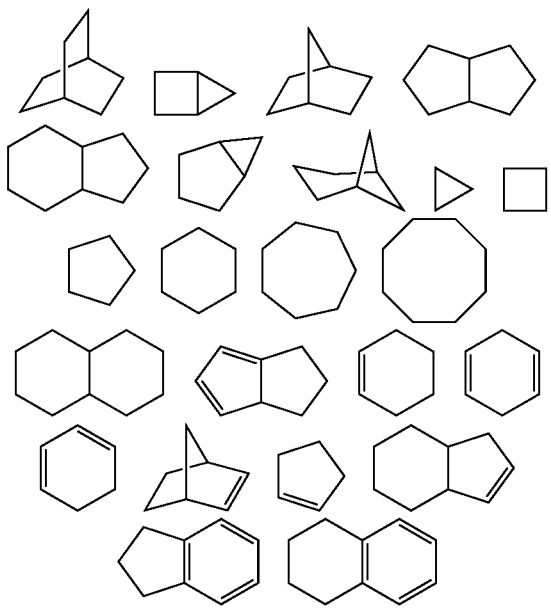

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "aromatic" refers to a carbocycle or heterocycle with one or more polyunsaturated rings and having aromatic character, i.e., having (4n+2) delocalized π (pi) electrons, where n is an integer.

The terms "aryl" or "arylene" are used interchangeably herein, and when employed alone or in combination with other terms, mean, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is one of aryl-$CH_2$—, aryl-$CH(CH_3)$—, and aryl-CH3. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

The terms "unsaturated or saturated aliphatic moiety of short chain fatty acid," "unsaturated or saturated aliphatic moiety of medium chain fatty acid" and "unsaturated or saturated aliphatic moiety of long chain fatty acid" as used herein refer to the aliphatic (saturated or unsaturated) tail, which is bonded to the carboxylic acid moiety of a fatty acid. It is known to those skilled in the art that a fatty acid comprises a carboxylic acid moiety (C(=O)OH) which is bonded to a saturated or unsaturated aliphatic carbon chain, which contains between, for example, 2 carbon atoms to 5 carbon atoms for a short chain fatty acid, 6 carbon atoms to 12 carbon atoms for a medium chain fatty acid, 13 carbon atoms or longer for a long chain fatty acid, and 22 carbon atoms or longer for a very long chain fatty acid. For example, caprylic acid is a fatty acid containing a carboxyl moiety bonded to a saturated 7-carbon aliphatic chain. As such, the fatty acid caprylic acid ($CH_3(CH_2)_6COOH$) comprises a carboxylic acid moiety and a seven-carbon hydrocarbon chain. Stearic acid ($CH_3(CH_2)_{16}COOH$) contains a seventeen-carbon hydrocarbon chain bonded to a carboxylic acid moiety. An unsaturated hydrocarbon chain refers to a chain possessing one or more, optionally one to six, double and/or triple bonds present within the hydrocarbon chain. In one embodiment, the stereochemistry of the unsaturation in the long chain is all cis, all trans, or a mixture thereof.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —$NH_2$, —OH, —NH($CH_3$), —N($CH_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

The terms "unsaturated or saturated aliphatic moiety of short chain fatty acid", "unsaturated or saturated aliphatic moiety of medium chain fatty acid" and "unsaturated or saturated aliphatic moiety of long chain fatty acid" as used herein refer to the aliphatic (saturated or unsaturated) tail which is bonded to the carboxylic acid moiety of a fatty acid. It is known to those skilled in the art that a fatty acid comprises a carboxylic acid moiety (C(=O)OH) which is bonded to a saturated or unsaturated aliphatic carbon chain, which contains between, for example, 2 carbon atoms to 5 carbon atoms for a short chain fatty acid, 6 carbon atoms to 12 carbon atoms for a medium chain fatty acid, 13 carbon atoms to 21 carbon atoms for a long chain fatty acid, and longer than 22 carbons for a very long chain fatty acid. For example, caprylic acid is a fatty acid containing a carboxyl moiety bonded to a saturated 7-carbon aliphatic chain. As such, the fatty acid caprylic acid (CH$_3$(CH$_2$)$_6$COOH) comprises a carboxylic acid moiety and a seven-carbon hydrocarbon chain. Stearic acid (CH$_3$(CH$_2$)$_{16}$COOH) contains a seventeen-carbon hydrocarbon chain bonded to a carboxylic acid moiety. An unsaturated hydrocarbon chain refers to a chain possessing one or more, optionally one to six, double and/or triple bonds present within the hydrocarbon chain. In one embodiment, the stereochemistry of the unsaturation in the long chain is all cis, all trans, or a mixture thereof.

As used here, the terms "N-acetylglucosamine" and "GlcNAc" are interchangeable and refer to 2-(acetylamino)-2-deoxy-D-glucose.

As used herein, the term "G-6-A" refers to N-acetylglucosamine 6-acetate.

As used herein, the term "G-3-A" refers to N-acetylglucosamine 3-acetate.

As used herein, the term "G-4,6-DA" refers to N-acetylglucosamine 4,6 diacetate.

As used herein, the term "G-3,4-DA" refers to N-acetylglucosamine 3,4 diacetate.

As used herein, the term "G-3,6-DA" refers to N-acetylglucosamine 3,6 diacetate.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates in part to the unexpected discovery of analogues of N-acetylglucosamine (GlnNAc) that increase the amount of branched N-glycans in a subject. In one aspect, the compounds of the invention may be used to treat or prevent a disease or disorder associated with low levels of branched N-glycans in a subject in need thereof. In one embodiment, the disease or disorder is an autoimmune disorder. In one embodiment, the disease or disorder is multiple sclerosis (MS). In another embodiment, the disease or disorder is rheumatoid arthritis (RA).

Figure 2:
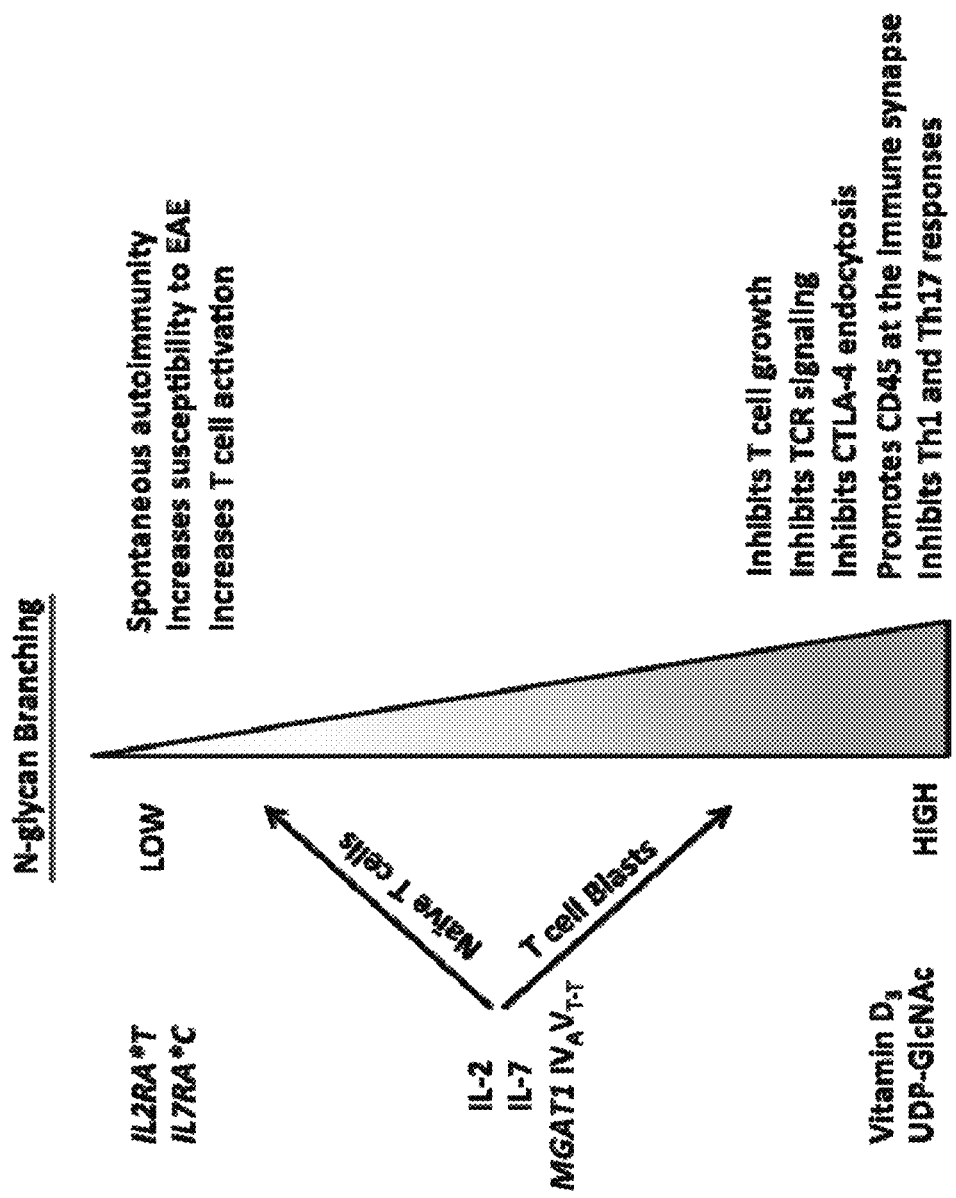
FIG. 2 is a diagram illustrating how genetic risk factors for MS, (IL-7RA*T, IL-2RA*C), and environmental factors for MS (vitamin $D_3$ and UDP-GlcNAc), combine with IL-2, IL-7, and MGAT1 IVA VT-T to contribute to low or high levels of N-glycan branching. Low levels of N-glycan branching result in spontaneous autoimmunity, increased susceptibility to experimental autoimmune encephalomyelitis (EAE), and increased T cell activation, whereas high levels of N-glycan branching result in inhibition of T cell growth, inhibition of TCR signaling, inhibition of CTLA-4 endocytosis, promotion of CD45 at the immune synapse, and inhibition of Th1 and Th17 responses. IL-2 and IL-7 both decrease branching in naïve T cells and increase branching in T cell blasts.

In complex trait diseases, such as MS, RA, and type 1 diabetes, multiple genetic and environmental factors can combine to determine disease risk. Yet identifying how genetic and environmental factors combine to give rise to disease-promoting molecular effects has been a great challenge. A role for genetics in MS was identified in studies that showed first-degree relatives of individuals that have MS and identical twins of individuals that have MS display from approximately 40-fold up to approximately 300-fold increased MS risk, respectively, over the general population. Also, candidate gene studies have identified an association between MS with genes in the MHC region. Genome wide association studies (GWAS) have identified a number of genes potentially associated with MS, including receptors for IL-7 (IL-7RA) and IL-2 (IL-2RA) (FIGS. 1 and 2). GWAS have further identified MGAT5, a gene encoding an enzyme in the Asn (N)-linked protein glycosylation pathway, as a gene that affects MS severity.

Although some potential genetic risk factors for MS have been identified, critical issues remain unsolved. For example, most genetic risk factors identified as associated with MS only confer relatively small increases in disease risk and explain only a small proportion of the genetic variance observed in risk for MS and predisposition for MS. Furthermore, monozygotic twins co-develop MS only approximately 30% of the time, which implies that there is a direct environmental impact on genetic risk for MS. Without being limited to any particular theory, these observations may be explained by epistatic and/or additive interactions between multiple alleles and environmental factors for MS that converge to effect molecular changes associated with MS, such as decreased branched N-glycan levels (FIG. 1). Consistent with this hypothesis, multiple genetic variants associated with MS risk (e.g., IL-7RA, IL-2RA, MGAT1, and CTLA-4) interact with multiple environmental factors (vitamin D$_3$ deficiency and metabolism) to dysregulate N-glycosylation levels in MS (FIGS. 1 and 2).

Figure 3:
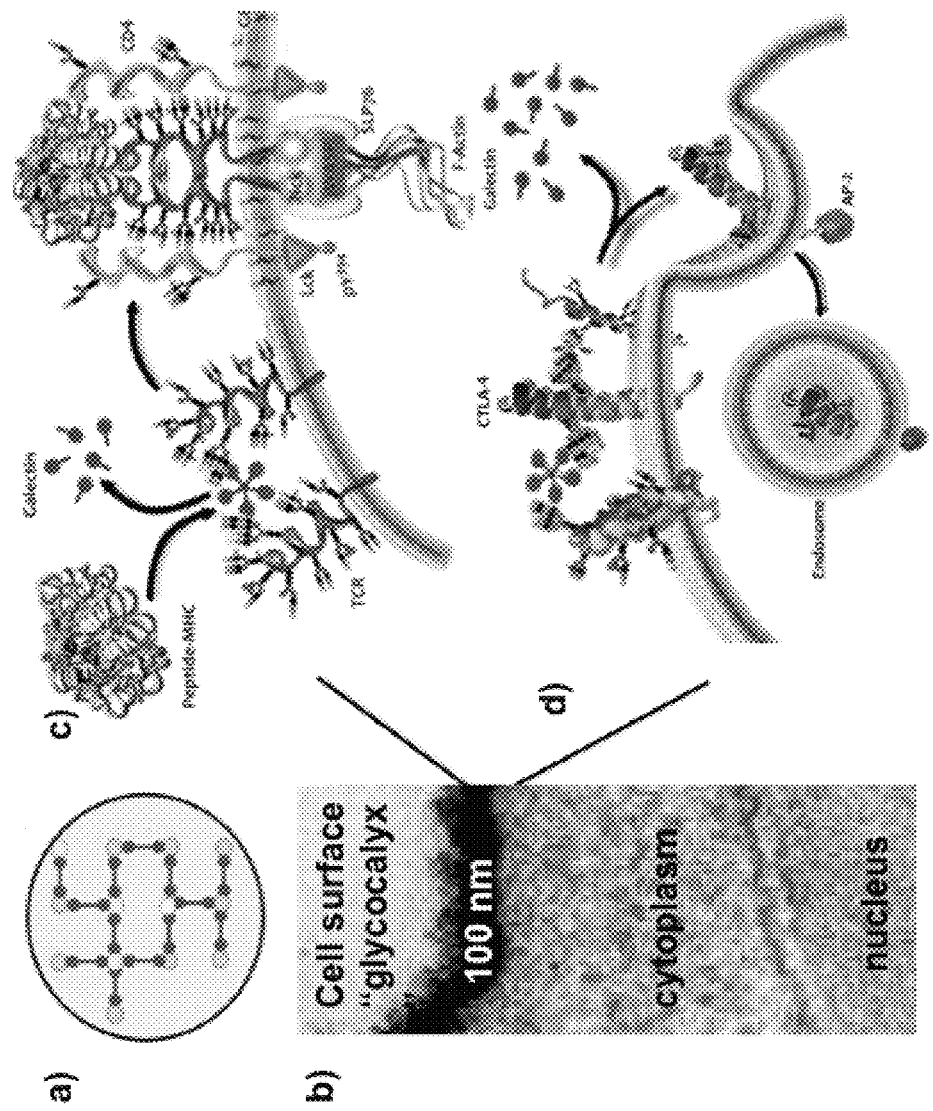
FIG. 3, comprising
Figure 4:
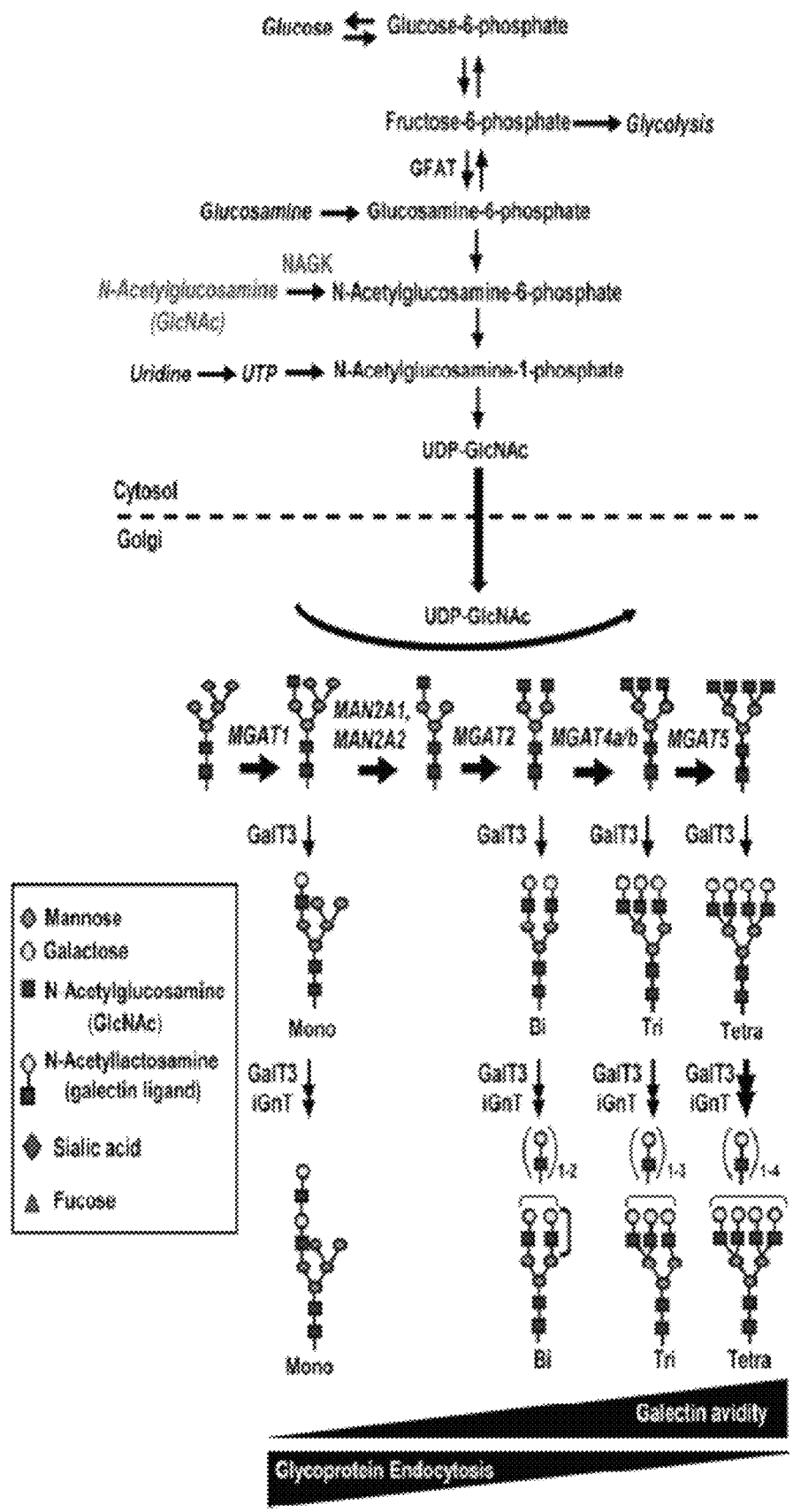
FIG. 4 is a schematic illustrating the regulation of N-acetylglucosamine (GlcNAc)-branched N-glycan biosynthesis by the hexosamine and N-glycan pathways. Uridine diphosphate N-acetylglucosamine (UDP-GlcNAc) is required by the N-acetylglucosaminyltransferases Mgat1, 2, 4, and 5 and iGnT. Cytosolic UDP-GlcNAc enters the Golgi via antiporter exchange with Golgi uridine 5'-monophosphate (UMP), a reaction product of the N-acetylglucosaminyltransferases. Galectins bind N-acetyllactosamine, with avidity increasing in proportion to the number of N-acetyllactosamine units (i.e., branching). β1,6-GlcNAc branching by Mgat5 promotes poly-N-acetyllactosamine production, further enhancing avidity for galectins, although poly-N-acetyllactosamine extension is possible on all branches. GalT3, galactosyltransferase 3; NAGK, N-acetylglucosamine kinase; GFAT, glutamine fructose-6-phosphate amidotransferase.
Figure 5:
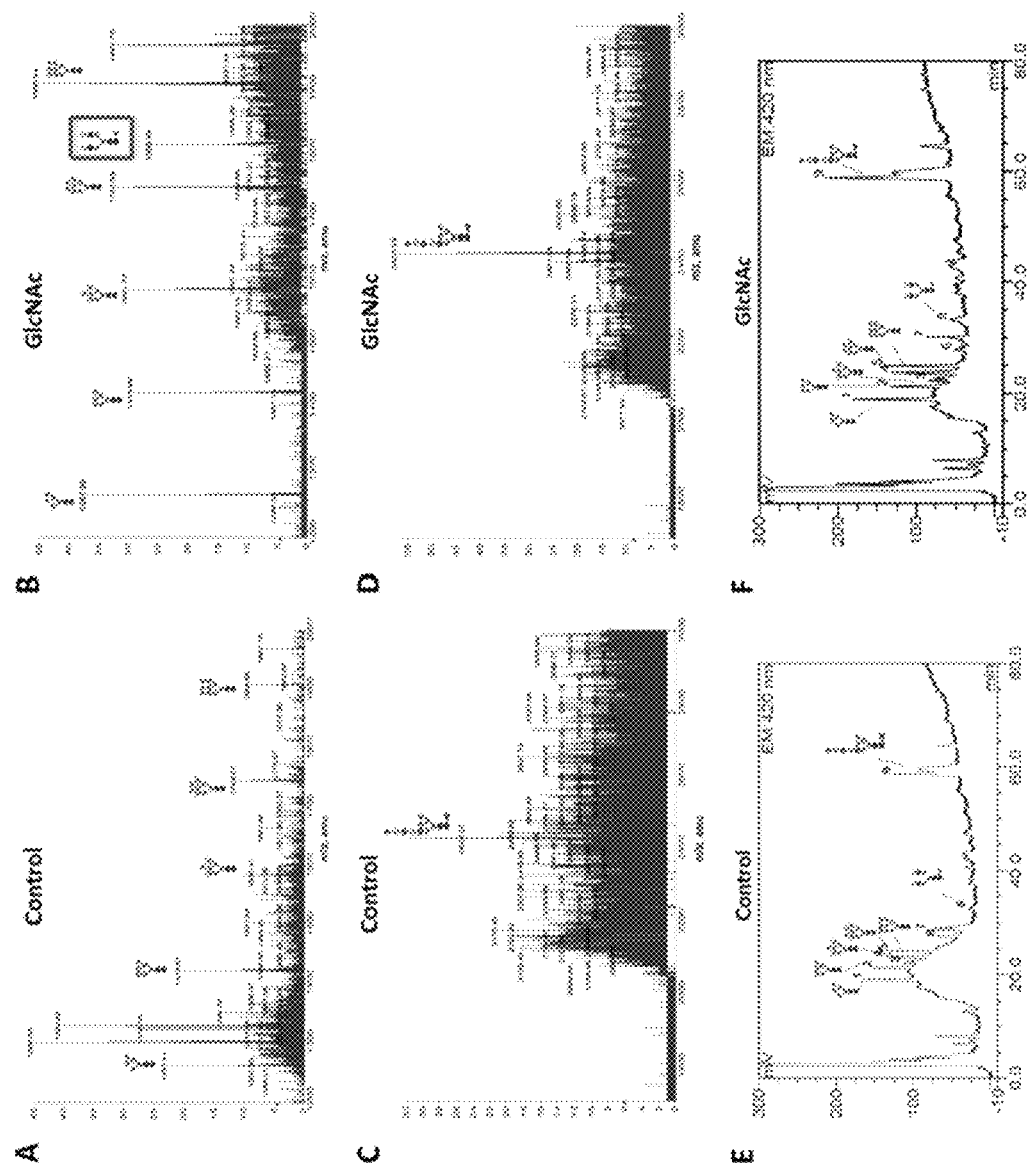
FIG. 5, comprising
Figure 6:
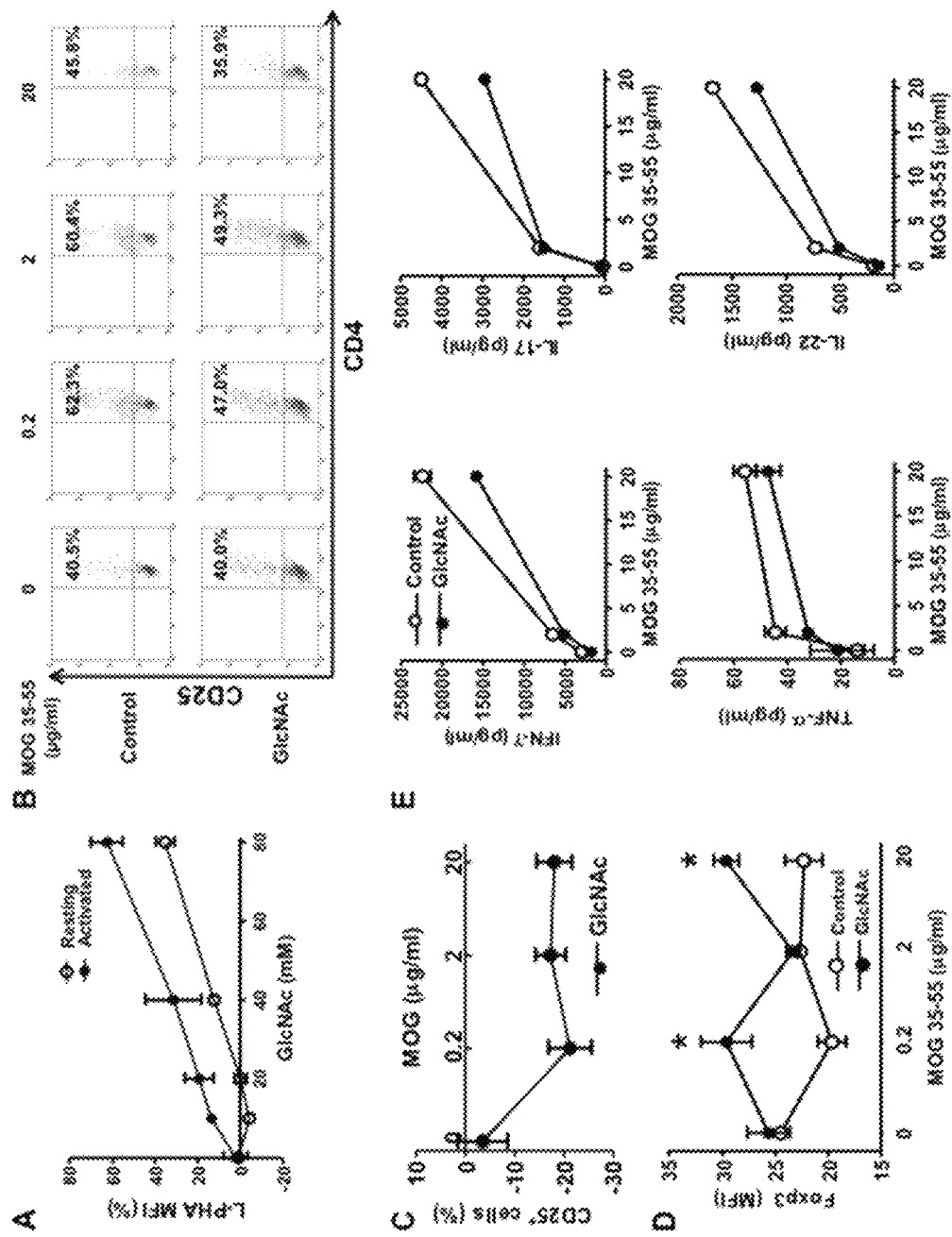
FIG. 6, comprising

N-glycan branching by the Golgi enzymes Mgat1, 2, 4 and 5 can promote increased production of N-acetyllactosamine, ligand for the galectin family of carbohydrate-binding proteins (FIG. 4). Galectins can bind N-glycans attached to surface glycoproteins to form molecular "lattices" at the cell surface, which may be involved in regulating clustering and endocytosis of transmembrane receptors and/or transporters with effects on cell growth and differentiation (FIG. 3). In T cells, N-glycan branching can inhibit basal and activation signaling through the T cell receptor (TCR) and CD45, promote growth arrest by CTLA-4 and TGFβ receptor, and enhance anti-inflammatory T-helper-2 (TH2) differentiation over pro-inflammatory TH1/TH17 differentiation. Metabolically increasing substrate UDP-GlcNAc to Golgi enzymes, by supplementing T cells in vitro with GlcNAc, can enhance N-glycan branching, suppress T cell growth, promote anti-autoimmune CTLA-4 and TGFβ receptor expression, block pro-autoimmune TH1 and TH17 differentiation, and enhance anti-autoimmune T-regulatory (Treg) and TH2 differentiation (FIGS. 5 and 6). The ability of GlcNAc to simultaneously inhibit critical pro-autoimmune phenotypes (e.g., T cell growth, TH1/TH17 responses) while enhancing critical anti-autoimmune phenotypes (e.g., CTLA-4, TGFI3 receptor, Treg, and TH2) makes it a potential treatment for autoimmune disorders. For example, GlcNAc treatment of myelin-reactive T cells in vitro inhibited EAE when these cells were adoptively transferred into naïve mice. In addition, orally administered GlcNAc can suppress spontaneous autoimmune diabetes in non-obese diabetic mice when initiated prior to disease onset.

Genetic data in mice and humans indicates N-glycan branching plays a role in autoimmune demyelinating disease pathogenesis and progression. For instance, IL2RA and IL7RA MS risk variants alter N-glycan branching by blocking IL-2 and IL-7 signaling-mediated changes in MGAT1, a Golgi gene product upstream of MGAT5. Moreover, an MS-associated variant of MGAT1 interacts with multiple MS modulators to control N-glycan branching and MS risk, including the IL2RA and IL7RA MS risk variants and vitamin D3. Vitamin D3 inversely associates with MS, regulates MGAT1 at least by increasing mRNA expression thereof, and inhibits EAE by promoting N-glycan branching. Mgat5 deficiency in 129/Sv mice results in enhanced susceptibility to EAE and spontaneous kidney autoimmunity.

Several mouse strains highly susceptible to EAE (PL/J, SJL, and NOD) display N-glycan branching deficiency in T cells compared with resistant strains (129/Sv, BALB/c, and B10.S). The PL/J strain displays the lowest levels, with a small minority developing spontaneous late onset motor weakness characterized by inflammatory demyelination, neuronophagia, and axonal damage in demyelinated lesions and otherwise normal appearing white matter; phenotypes markedly enhanced by Mgat5$^{+/-}$ and Mgat5$^{-/-}$ genotypes in a gene dose-dependent manner. N-Glycan branching in neurons directly controls neuronal survival independent of inflammation, as neuron-specific deficiency of MGAT1 in mice results in spontaneous neuronal apoptosis in vivo and neurological deficits.

Figure 7:
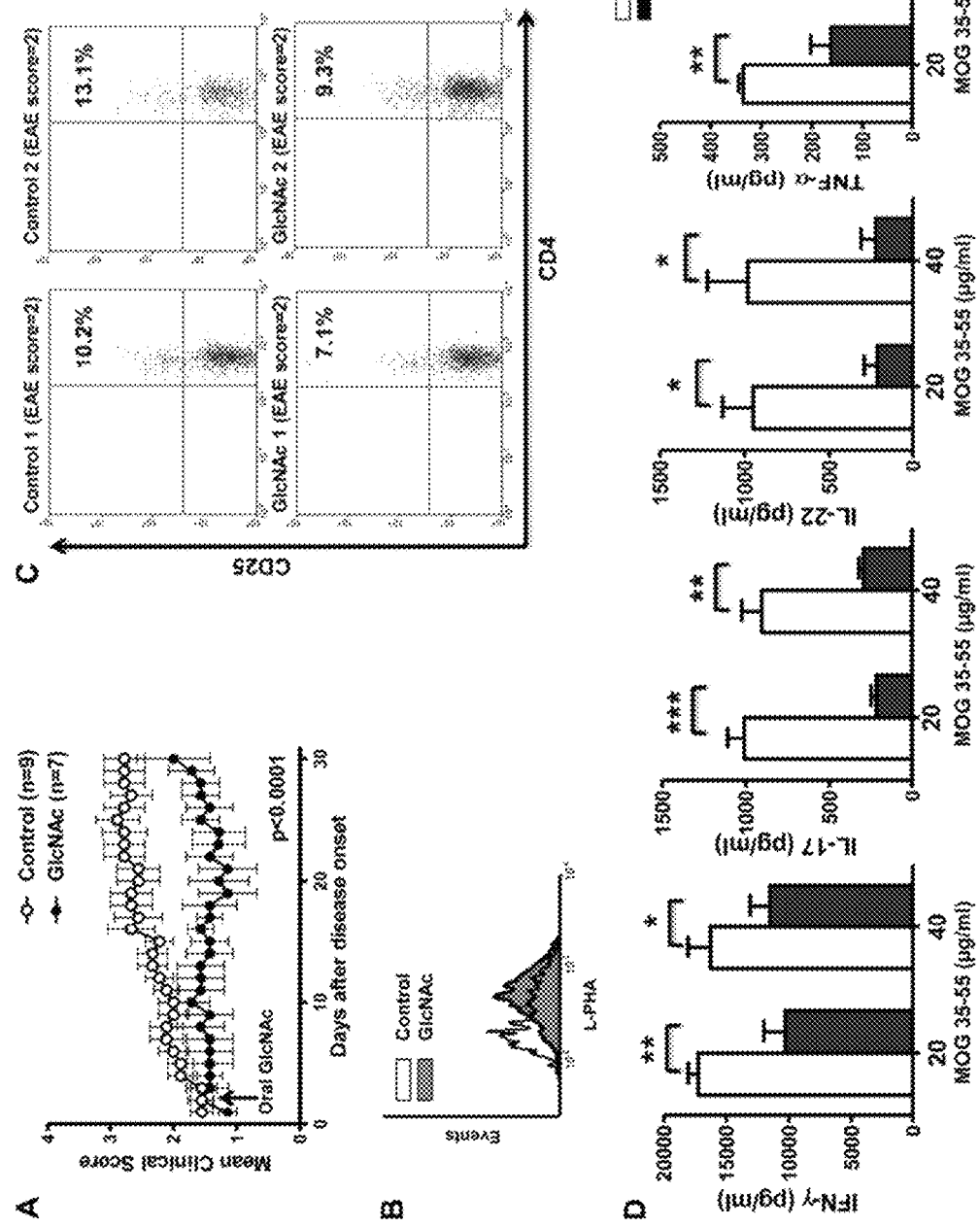
FIG. 7, comprising
Figure 8:
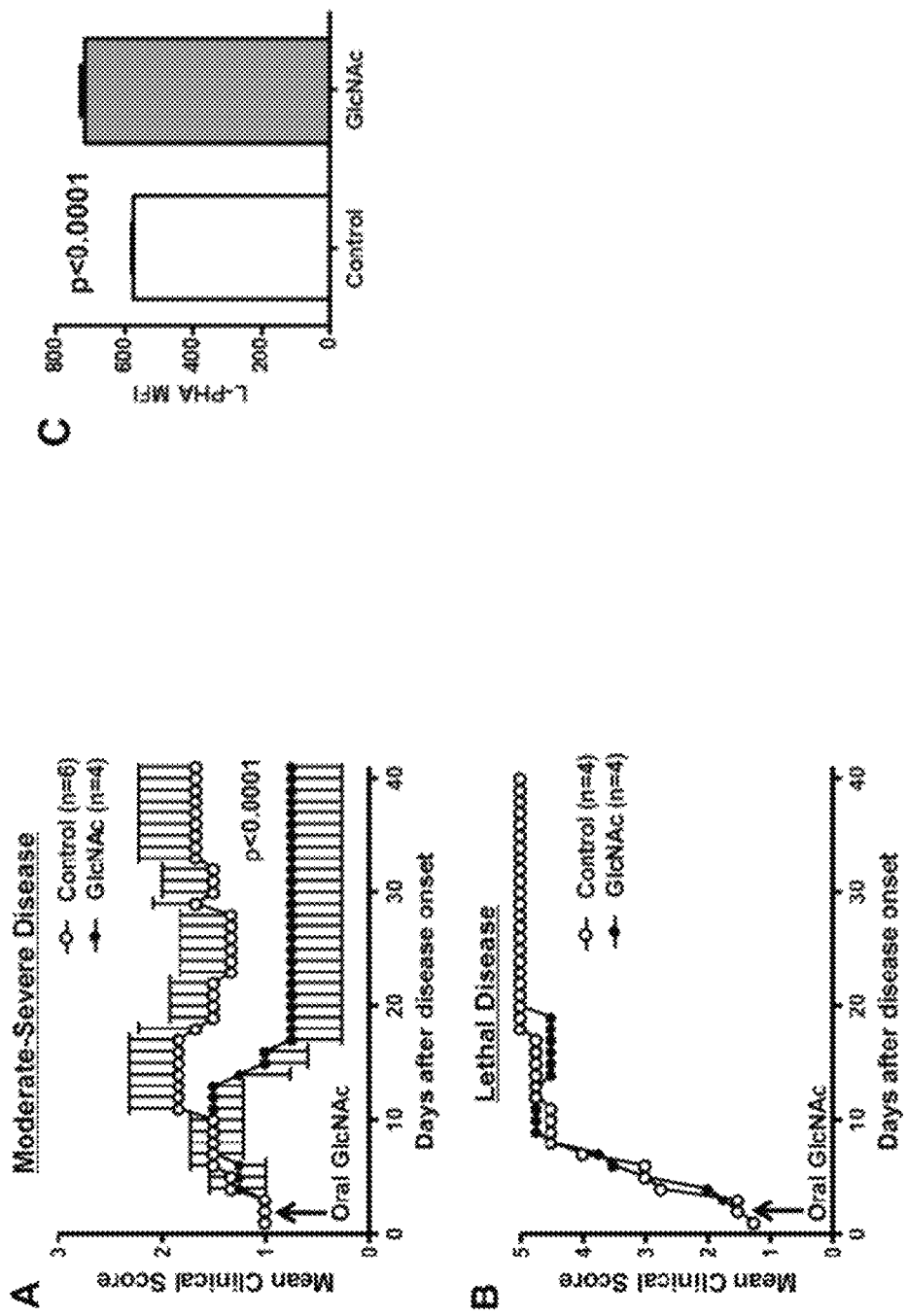
FIG. 8, comprising

When initiated after disease onset, oral GlcNAc administration inhibited EAE progression and down-regulated pro-autoimmune TH1 and TH17 responses while increasing Treg levels in vivo (FIGS. 7 and 8). In humans, in vitro GlcNAc rescued N-glycan branching deficiency and T cell hyper-proliferation in peripheral blood mononuclear cells induced by the MS-associated MGAT1 variant. Finally, a pilot study of oral GlcNAc in pediatric treatment-resistant inflammatory bowel disease patients reported that 8 of 12 children went into clinical remission for approximately 2 years with evidence of histological improvement. GlcNAc appears to be safe, as it has been used as a supplement for many years without reported adverse effects and large-dose intravenous administration in humans. And chronic systematic toxicological studies in animals have demonstrated no associated toxicity.

Glucosamine enters cells more efficiently than GlcNAc, via the glucose transporter. While glucosamine may increase UDP-GlcNAc to enhance N-glycan branching, it also fluxes into the glycolytic pathway for ATP production (FIG. 4). In contrast, GlcNAc does not enter glycolysis, nor does it enter the pentose phosphate pathway or the TCA cycle; it is exclusively utilized for UDP-GlcNAc production. However, the effectiveness of glucosamine at increasing N-glycan branching was limited compared with GlcNAc, with increasing concentrations of glucosamine initially increasing but subsequently decreasing N-glycan branching. The latter would enhance T cell mediated autoimmunity and likely results from feedback inhibition. In contrast, increasing GlcNAc concentrations in vitro was observed to only enhance N-glycan branching.

Despite the beneficial properties of GlcNAc, it also possesses several drawbacks. For instance, the biological activity of GlcNAc is limited by low membrane permeability (poor cell entry), and GlcNAc requires relatively higher doses and plasma concentrations of GlcNAc to achieve desired effects. In addition, GlcNAc cannot utilize transporters to gain cell entry. Instead, it requires macropinocytosis and high membrane turnover to gain intracellular access.

In order to address the membrane permeability of GlcNAc, the tetraacetate analogue of GlcNAc was developed. GlcNAc-tetraacetate has increased membrane permeability as compared with GlcNAc. However, GlcNAc-tetraacetate has a large number of hydrophobic functional groups, and once inside the cell, it may not be efficiently converted by endogenous catabolic enzymes into GlcNAc, which may contribute to the observed increase in toxicity associated with its use.

In one aspect, the present invention provides analogs of GlcNAc that have surprisingly advantageous properties as compared with other compounds known in the art. In one embodiment, the compounds of the present invention have the above-discussed beneficial therapeutic effects of GlcNAc and GlcNAc-tetraacetate while simultaneously overcoming the above-discussed disadvantages of GlcNAc and GlcNAc-tetraacetate. In one embodiment, the compounds of the invention comprise GlcNAc modified with hydrophobic functional groups, such as acetyl and butyrate groups, at specific positions on the sugar ring, which has the effect of increasing the lipophilic properties, enhancing the cell entry, and limiting the cellular toxicity of the analogs of GlcNAc of the present invention as compared with either GlcNAc or GlcNAc-tetraacetate. In one embodiment, the compounds of the present invention have the surprisingly advantageous property of being efficiently converted to GlcNAc by endogenous catabolic enzymes. In one embodiment, the compounds of the invention increase N-glycan branching in vitro at several-fold lower concentrations than GlcNAc, while having low levels of toxicity.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I) or a salt or solvate thereof, and combinations thereof:

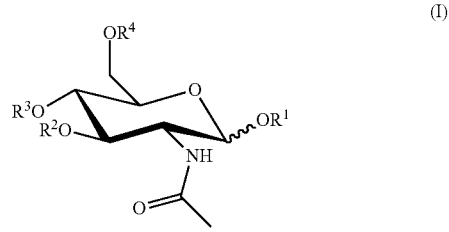

(I)

wherein:

$R^1$, $R^2$, $R^3$, and $R^4$ are each independently selected from the group consisting of H, C(O)R', $C_1$-$C_5$ alkyl, $C_2$-$C_5$ alkenyl, cycloalkyl, aryl, arylalkyl, and an unsaturated or saturated aliphatic moiety of a 6-carbon to 22-carbon medium- or a long chain fatty acid, wherein the alkyl, alkenyl, cycloalkyl, aryl, and arylalkyl group may be optionally substituted; and R' is selected from the group consisting of H, $C_1$-$C_5$ alkyl, $C_2$-$C_5$ alkenyl, cycloalkyl, aryl, arylalkyl, and an unsaturated or saturated aliphatic moiety of a 6-carbon to 21-carbon medium- or long chain fatty acid, wherein the alkyl, alkenyl, cycloalkyl, aryl, and arylalkyl group may be optionally substituted;

with the proviso that at least one of $R^1$, $R^2$, $R^3$, and $R^4$ is not H, and that $R^1$, $R^2$, $R^3$, and $R^4$ cannot simultaneously be C(O)Me.

In one embodiment, R' is selected from the group consisting of H, methyl, propyl, butyl, isobutyl, and an unsaturated or saturated aliphatic moiety of a 6-carbon to 21-carbon medium- or a long chain fatty acid. In one embodiment, R' is methyl.

In one embodiment, at least one of $R^1$, $R^2$, $R^3$, and $R^4$ is C(O)R'. In another embodiment, at least one of $R^1$, $R^2$, $R^3$, and $R^4$ is C(O)R', wherein R' is methyl. In another embodiment, one of $R^1$, $R^2$, $R^3$, and $R^4$ is C(O)R', wherein R' is methyl. In another embodiment, two of $R^1$, $R^2$, $R^3$, and $R^4$ are C(O)R', wherein both R' are methyl. In another embodiment, three of $R^1$, $R^2$, $R^3$, and $R^4$ are C(O)R', wherein all three R' are methyl. In one embodiment, one of $R^1$, $R^2$, $R^3$, and $R^4$ is C(O)R', and the rest are H In one embodiment, $R^1$ is C(O)R'. In another embodiment, $R^2$ is C(O)R'. In another embodiment, $R^3$ is C(O)R'. In another embodiment, $R^4$ is C(O)R'. In one embodiment, both $R^2$ and $R^3$ are C(O)R'. In another embodiment, both $R^2$ and $R^4$ are C(O)R'. In another embodiment, both $R^3$ and $R^4$ are C(O)R'. In one embodiment, $R^2$, $R^3$, and $R^4$ are each C(O)R'. In one embodiment, $R^1$, $R^2$, and $R^3$ are each H. In another embodiment, $R^1$, $R^3$, and $R^4$ are each H. In another embodiment, $R^1$, $R^2$, and $R^4$ are each H. In one embodiment, both $R^1$ and $R^4$ are H. In another embodiment, both $R^1$ and $R^3$ are H. In another embodiment, both $R^1$ and $R^2$ are H. In one embodiment, $R^1$ is H'.

In one embodiment, the compound is selected from the group consisting of:

N-acetylglucosamine 3-acetate,
N-acetylglucosamine 4-acetate,
N-acetylglucosamine 6-acetate,
N-acetylglucosamine 3,4 diacetate,
N-acetylglucosamine 3,6 diacetate,
N-acetylglucosamine 4,6 diacetate, and
N-acetylglucosamine 3,4,6 triacetate, a salt or solvate thereof, and any combinations thereof.

In one embodiment, the compound is N-acetylglucosamine 6-acetate, or a salt or solvate thereof.

In some embodiments, the compound of the invention is N-acetylglucosamine substituted with a hydrophobic group or lipophilic group. Examples of hydrophobic groups and lipophilic groups include, but are not limited to, substituted or unsubstituted, saturated or partially unsaturated $C_2$-$C_{24}$ alkyl groups, substituted or unsubstituted aryl, cycloalkyl, or arylalkyl groups, and esters such as fatty acid esters.

The compounds of formula (I) have an anomeric carbon in their structure. In one embodiment, the compounds of the invention include anomeric forms alpha (α) and beta (β), and their mixtures. In one embodiment, the compounds are a mixture of alpha and beta anomers at a ratio of about 1:1.

The invention also includes a pharmaceutical composition comprising at least one compound selected from formula (I).

Preparation of the Compounds of the Invention

Compounds of formula (I) may be prepared by the general schemes described herein, using the synthetic method known by those skilled in the art. The following examples illustrate non-limiting embodiments of the invention.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomers is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Methods of the Invention

The invention includes a method of treating or preventing a disease or disorder associated with low levels of branched N-glycans in a subject in need thereof. The method comprises administering to the subject a therapeutically effective amount of a pharmaceutical composition comprising a compound of the invention. In one embodiment, the method further comprises administering to the subject an additional therapeutic agent.

The invention also includes a method or preventing a disease or disorder associated with low levels of branched N-glycans in a subject in need thereof. The method comprises obtaining a sample of biological material containing genetic defects in N-glycosylation pathway genes from the subject, analyzing the polynucleotide sequences to detect the presence of known polymorphisms in N-glycosylation pathway/hexosamine genes associated with disease, and administering to the subject a therapeutically effective amount of a pharmaceutical composition comprising a compound of the invention.

In various embodiments, the disease or disorder is selected from the group consisting of multiple sclerosis (MS), autoimmune diabetes, pediatric treatment-resistant inflammatory bowel disease, rheumatoid arthritis (RA), systemic lupus erythematosus (SLE), autoimmune glomerulonephritis, acute disseminated encephalomyelitis, acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome, autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura, autoimmune thyroid disease, autoimmune urticarial, an axonal & neuronal neuropathy, Balo disease, Behcet's disease, bullous pemphigoid, cardiomyopathy, Castleman disease, celiac disease, Chagas disease, chronic inflammatory demyelinating polyneuropathy, chronic recurrent multifocal osteomyelitis, Churg-Strauss syndrome, cicatricial pemphigoid/benign mucosal pemphigoid, Crohn's disease, Cogan's syndrome, cold agglutinin disease, congenital heart block, coxsackie myocarditis, CREST disease, essential mixed cryoglobulinemia, a demyelinating neuropathy, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), glomerulonephritis, Goodpasture's syndrome, granulomatosis with polyangiitis (GPA; see Wegener's Graves' disease), Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, insulin-dependent diabetes (type1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), Lyme disease, chronic Meniere's disease, microscopic polyangiitis, mixed connective tissue disease, Mooren's ulcer, Mucha-Habermann disease, myasthenia gravis, myositis, narcolepsy, neuromyelitis optica (Devic's), neutropenia, ocular cicatricial pemphigoid, optic neuritis, palindromic rheumatism, pediatric autoimmune neuropsychiatric disorders associated with *Streptococcus* (PANDAS), paraneoplastic cerebellar degeneration, paroxysmal nocturnal hemoglobinuria, Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis *nodosa*, Type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reflex sympathetic dystrophy, Reiter's syndrome, relapsing polychondritis, restless legs syndrome, retroperitoneal fibrosis, rheumatic fever, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, and vitiligo.

In one embodiment, the disease or disorder is multiple sclerosis (MS). In another embodiment, the disease or disorder is rheumatoid arthritis (RA). In another embodiment, the disease or disorder is autoimmune diabetes. In another embodiment, the disease is pediatric treatment-resistant inflammatory bowel disease.

In one embodiment, administering the compound of the invention to the subject allows for administering a lower dose of the therapeutic agent as compared with the dose of the therapeutic agent alone that is required to achieve similar results in treating or preventing a low level of branched N-glycans in the subject. For example, in one embodiment, the compound of the invention enhances the activity of the additional therapeutic compound, thereby allowing for a lower dose of the therapeutic compound to provide the same effect.

In one embodiment, the compound of the invention and the therapeutic agent are co-administered to the subject. In another embodiment, the compound of the invention and the therapeutic agent are co-formulated and co-administered to the subject.

In one embodiment, the subject is a mammal. In another embodiment, the mammal is a human.

Combination Therapies

In some embodiments, the compositions of the present invention are useful in combination with one or more additional compounds. In one embodiment, the additional compound is also a compound of the invention. In another embodiment, the additional compound is glucosamine. In another embodiment, the additional compound is N-acetylglucosamine. In another embodiment, the additional compound is an analogue of N-acetylglucosamine. In one embodiment, the compound is N-acetylglucosamine tetraacetate. In one embodiment, the compound is an agonist of complex-branched N-glycans, a sugar donor for complex branched N-glycans, a metabolite of pathways for synthesis of the sugar nucleotide donor or precursors thereof, or regulators of agonists of a sugar donor or a pathway for the synthesis of a sugar donor, and any combination thereof. In one embodiment, the compound is Vitamin $D_3$. In one embodiment, the compound is a metabolite in the hexosamine pathway. In one embodiment, the compound is selected from the group consisting of glucose-6-phosphate, fructose-6-phosphate, glucosamine-6-phosphate, N-acetylglucosamine-6-phosphate, N-acetylglucose-1-phosphate, and UDP-GlcNAc.

In one embodiment, the agonist of complex-branched N-glycans is an agonist of Mgat5. In one embodiment, the agonist of Mgat5 increases the expression Mgat5 polynucleotides, in particular Mgat5 mRNA. Examples of agonists of Mgat5 expression include, but are not limited to, insoluble lipid vitamins agonists such as Vitamin $D_3$, retinoic acid, analogs and derivatives thereof, and the like. Examples of Vitamin $D_3$ analogues include, but are not limited to, 1-hydroxy Vitamin D3 and 1,25 dihydroxy-Vitamin $D_3$.

A sugar donor may be a nucleotide sugar, dolichol-phosphate-sugar or dolichol-pyrophosphate-oligosaccharide, for example, cytidine or uridine diphospho-N-acetylglucosamine (CDP-GlcNAc or UDP-GlcNAc).

Metabolites for use in the methods of the invention include without limitation one or more of nucleotides (e.g., UMP, UDP, UTP, CMP, CDP, CTP), nucleosides (e.g., cytidine,uridine), nucleobases (e.g., uracil, cytosine), sugars (e.g., glucose), and analogs and derivatives thereof, and hexosamine pathway supplements such as glucosamine, N-acetylglucosamine (GlcNAc), uridine, acetyl coA, $NH_4^+$, glutamine, and glucose, or derivatives or analogs thereof.

In one embodiment, a sugar donor comprises one or more metabolites, wherein the metabolite is selected from the group consisting of nucleotides (e.g., UMP, UDP, UTP, CMP, CDP, or CTP); nucleosides (e.g., cytidine or uridine), nucleobases (e.g., uracil, cytosine), sugars (e.g., glucose), acetoacetate, glutamine, glucosamine or GlcNAc or analogs and derivatives thereof.

In one embodiment, the metabolites comprise a nucleotide, nucleoside, nucleobase, a sugar, and/or a combination of a nucleotide, nucleoside, nucleobase, and a sugar, such as uridine or cytidine and a sugar, UDP, uracil, uridine, GlcNAc, and/or analogs or derivatives thereof.

In one embodiment, an analogue or derivative of a metabolite is used. For example, an acetylated GlcNAc, peracetylated GlcNAc, or GlcNAc tetraacetate (e.g., N-acetyl-beta-D-glucosamine tetraacetate or alpha-D-N-acetylglucosamine tetraacetate) may be used.

In certain embodiments, these additional compounds may comprise therapeutic agents known to treat or prevent a disease or disorder associated with low levels of branched N-glycans. Such compounds include, but are not limited to, agents used for the treatment of multiple sclerosis (MS), disease-modifying antirheumatic drugs (DMARDs), immunosuppressive agents, analgesics, intravenous immunoglobulin (IVIG), anti-inflammatory agents, neutraceuticals such as vitamins and supplements, and the like.

In non-limiting examples, the compositions of the invention may be used in combination with one or more therapeutic agents (or a salt, solvate or prodrug thereof).

In certain embodiments, the compositions of the invention may be administered to a subject in conjunction with (e.g., before, simultaneous, or after) an agent used for the treatment of multiple sclerosis (MS) such as glatiramer acetate (Copaxone®), a β-Interferon such as Avonex (interferon β-1a), Rebif (interferon β-1a), Plegridy (peginterferon β-1a), Betaseron and Extavia (interferon β-1b), fingolimod (Gilenya®), teriflunomide (Aubagio®), dimethyl fumarate (Tecfidera®), alemtuzumab (Lemtrada®), mitoxantrone (Novantrone®), natalizumab (Tysabri®), and dalfampridine (Ampyra®).

In certain embodiments, the compositions of the invention may be administered to a subject in conjunction with (e.g., before, simultaneous, or after) a DMARD such as cyclophosphamide, mycophenolate, methotrexate (MTX), leflunomide, abatacept, adalimumab, azathioprine, chloroquine, hydroxychloroquine, ciclosporin (Cyclosporin A), D-penicillamine, etanercept, golimumab, gold salts (sodium aurothiomalate, auranofin), belimumab, infliximab, leflunomide, methotrexate (MTX), minocycline, rituximab, and sulfasalazine (SSZ), in combination or independently. Non-limiting examples of DMARDs useful for the treatment of lupus include cyclophosphamide, mycophenolate, azathioprine, methotrexate, leflunomide and belimumab.

In certain embodiments, the compositions of the invention may be administered to a subject in conjunction with (e.g., before, simultaneous, or after) an immunosuppressive agent such as methothrexate, leflunomide, cyclophosphamide, cytoxan, lmmuran, cyclosporine A, minocycline, azathioprine, antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators, in combination or independently.

In certain embodiments, the compositions of the invention may be administered to a subject in conjunction with (e.g., before, simultaneous, or after) an analgesic such as opiates, opioids, morphine, codeine, oxycodone, hydrocodone, dihydromorphine, pethdine, paracetamol, acetaminophen, COX-2 inhibitors, Flupirtine, cyclooxygenase inhibitors and non-steroidal anti-inflammatory drugs (NSAIDs) such as acetyl salicylic acid, ibuprofen and naproxen, peripheral analgesic agents, and narcotic analgesics. Non-limiting examples of additional analgesics include capsaicin, lidocaine, bupivacaine, mepivacaine, ropivacaine, tetracaine, etidocaine, chloroprocaine, prilocalne, procaine, benzocaine, dibucaine, dyclonine hydrochloride, pramoxine hydrochloride and proparacaine. Other agents employed for the treatment of neuropathic pain which may be used in the methods and compositions of the invention include ketamine (an NMDA receptor antagonist), amitriptyline (a tricyclic antidepressant), gabapentin or pregabalin (α2δ calcium channel agents) and guanethidine (a sympathetic blocking agent), in combination or independently.

In certain embodiments, the compositions of the invention may be administered to a subject in conjunction with (e.g., before, simultaneous, or after) intravenous immunoglobulin (IVIG).

In certain embodiments, the compounds of the invention may be administered to a subject in conjunction with (e.g. before, simultaneously, or following) an anti-inflammatory agent selected from the group consisting of nonsteroidal agents ("NSAIDS") such as salicylates (e.g., salsalate, mesalamine, diflunisal, choline magnesium trisalicylate), diclofenac, diflunisal, etodolac, fenoprofen, flurbiprofen, ibuprofen, indomethacin, mefenamic acid, nabumetone, naproxen, piroxicam, phenyl butazone, ketoprofen, S-ketoprofen, ketorolac tromethamine, sulindac, tolmetin). Other anti-inflammatory drugs include steroidal agents such as beclomethasone, betamethasone, cortisone, dexamethasone, fluocinolone, flunisolide, fluticasone proprionate, fluorinated-corticoids, triamcinolone-diacetate, hydorcortisone, prednisolone, methylprednisolone, and prednisone, immunosuppressive agents (e.g., adenocorticosteroids, cyclosporin), antihistamines and decongestants (e.g., astemizole(histamine III-receptor antagonist), azatidine, brompheniramine, clemastine, chloφheniramine, cromolyn, cyproheptadine, diphenylimidazole, diphenhydramine hydrochloride, hydroxyzine, glycyrrhetic acid, homochlorocyclizine hydrochloride, ketotifen, loratadine, naphazoline, phenindamine, pheniramine, promethazine, terfenadine, trimeprazine, tripelennamine, tranilast, and the decongestants phenylpropanolamine and pseudoephedrine.

In certain embodiments, co-administration of a composition of the invention with one or more other therapeutic agents has a synergistic effect. A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The invention also includes a method of treating or preventing a disease or disorder associated with low levels of branched N-glycans in a subject in need thereof, wherein the method comprises administering to the subject an effective amount of a pharmaceutical composition comprising a compound of the invention and an additional therapeutic agent.

In one embodiment, when the compound of the invention is administered to the subject, a lower dose of the additional therapeutic agent can be administered therewith, as compared with the dose of the additional therapeutic agent used alone. In one embodiment, the compound of the invention and the additional therapeutic agent are co-administered, i.e., simultaneously to the subject but in separate formulations. In another embodiment, the compound of the invention and the additional therapeutic agent are co-formulated and are co-administered to the subject. In yet another embodiment, the compound of the invention and the additional therapeutics are administered separately to the subject, where one compounds is administered before the other.

In one embodiment, the therapeutically effective amount of a compound of the invention and an additional compound is a ratio of 1:20; 1:15; 1:10; 1:5:1:2.5:1:1; 2.5:1; 5:1; 10:1; 15:1; and 20:1 w/w (weight/weight), respectively, and is administered to the subject in a single dose or multiple doses over the course of a day, a week, a month, a year, or more.

Administration/Dosage/Formulations

The regimen of administration may affect what constitutes an effective amount. The therapeutic formulations may be administered to the subject either before or after the onset of a disease or disorder associated with low levels of branched N-glycans. Further, several divided dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, (e.g., human), may be carried out using known procedures, at dosages and for periods of time effective to treat a disease or disorder associated with low levels of branched N-glycans in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder associated with low levels of branched N-glycans in the patient. Dosage regimens may be adjusted to provide the optimum therapeutic response. For example, several divided doses may be administered daily. In another example, the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to assess the relevant factors and make the determination regarding the effective amount of the therapeutic compound without undue experimentation.

Actual dosage levels of the active ingredients in the pharmaceutical compositions of this invention may be varied to obtain an amount of the active ingredient that is effective to achieve the desired therapeutic response for a particular patient, composition, and mode of administration, without generating excessive side effects in the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical professional, e.g., physician or veterinarian, having ordinary skill in the art may readily determine and prescribe the effective amount of the pharmaceutical composition required. For example, the physician or veterinarian could start with a dosage of the compound of the invention in the pharmaceutical composition at a level that is lower than the level required to achieve the desired therapeutic effect, and then increase the dosage over time until the desired effect is achieved.

In particular embodiments, it is advantageous to formulate the compound in dosage unit form for ease of administration and uniformity of dosage. "Dosage unit form" as used herein refers to a physically discrete unit containing a predetermined quantity of therapeutic compound calculated to produce the desired therapeutic effect, in association with the required pharmaceutical vehicle. The dosage unit forms of the invention can be selected based upon (a) the unique characteristics of the therapeutic compound and the particular therapeutic effect to be achieved, and (b) the limitations inherent in the art of compounding/formulating such a therapeutic compound for the treatment of a disease or a disorder associated with low levels of branched N-glycans in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol or sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the patient, the current medical condition of the patient and the severity of the disease or disorder associated with low levels of branched N-glycans in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the invention for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the patient from about one to about five times per day or more. In various embodiments, the compositions of the invention are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a compound of the invention, alone or in combination with a second pharmaceutical agent; and instructions for using the compound to treat or prevent a disease or disorder associated with low levels of branched N-glycans in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

FIG. 5 shows matrix-assisted laser desorption/ionization—time of flight (MALDI-TOF) mass spectra and high-performance anion exchange chromatography (HPAEC)N- glycan profiles. The so-profiled N-glycans were isolated from purified CD3⁺T cells obtained from age and sex matched wild-type control mice or wild-type mice treated orally with GlcNAc for 7 days and analyzed by MALDI-TOF mass spectrometry (FIGS. 5A-5D) or HPAEC (FIGS. 5E and 5F). Abbreviations for individual sugars depicted in FIG. 5 are the same as those defined in FIG. 4. The CD3⁺T cells used in the MALDI-TOF and HPAEC were obtained from mice orally administered GlcNAc by supplementing their drinking water with 0.25 mg/ml GlcNAc, with intake confirmed by measuring the amount of drinking water consumed. 6 mice were used per group (i.e., control and GlcNAc treated), and the harvested CD3⁺T cells were pooled prior to analyses. The assignment of likely structures in the MALDI-TOF spectrum is based on mass and those in HPAEC on N-glycan standards from RNase B, IgG, and fetuin and correlations with the major structures observed in the MALDI-TOF spectrum. Definitive structure assignment of the latter requires HPAEC-mass spectrometry in-line as well as linkage analysis.

Example 2

The data plotted in FIG. 6A was obtained from experiments in which splenocytes were isolated from mice and cultured in vitro with the indicated concentrations of GlcNAc under resting or activated (1000 ng/ml anti-CD3) conditions for 3 days, stained with L-PHA-FITC in triplicate, and analyzed by FACS. The data plotted in FIGS. 6B-6E were obtained from experiments in which mice were immunized with the indicated amounts of MOG 35-55 peptide emulsified in Complete Freund's adjuvant and treated with GlcNAc at the same time by supplementing their drinking water at 0.25 mg/ml GlcNAc and control mice that were immunized with the indicated amounts of MOG 35-55 peptide but not treated with GlcNAc. After 14 days, splenocytes harvested from mice treated with GlcNAc had reduced CD25⁺T cells upon re-stimulation with MOG 35-55 peptide in culture (FIGS. 6B and 6C) and promoted development of CD4⁺CD25⁺FoxP3⁺ regulatory T cells (FIG. 6D), as compared with control mice. Although not wishing to be bound by any particular theory, the reduction in CD25⁺T cell blasts at the highest antigen concentrations is consistent with the explanation that the reduction is secondary to the observed increase in cell death, consistent with antigen-induced cell death at high antigen stimulation levels. FIG. 6E shows graphs that plot IFN-γ; TNF-α; IL-17; or IL-22 concentrations in CD3⁺T cells isolated from control and GlcNAc treated mice as a function of various concentrations of MOG 35-55 immunization. FIG. 6E indicates that oral GlcNAc treatment in vivo inhibited secretion of Th1 cytokines (IFN-γ and TNF-α) and Th17 cytokines (IL-17 and IL-22) upon re-stimulation with MOG 35-55 peptide in vitro.

Example 3

The data plotted in FIG. 7A was obtained from experiments in which EAE was induced in C57BL/6 mice by immunization with MOG 35-55 peptide emulsified in Complete Freund's adjuvant and pertussis toxin. GlcNAc mice were treated orally with GlcNAc by supplementing the drinking water at 0.25 mg/ml starting on the second day after disease onset and continued for the duration of the study and control mice were given drinking water not supplemented with GlcNAc (n=9 per control group, n=7 per GlcNAc group). Day 1 indicates the first day of disease onset. Mice were examined daily for clinical signs of EAE over the next 30 days with the observer blinded to treatment conditions and scored daily as follows: 0, no disease; 1, loss of tail tone; 2, hindlimb weakness; 3, hindlimb paralysis; 4, forelimb weakness or paralysis and hindlimb paralysis; 5, moribund or dead. Mean clinical scores per group daily were compared by the Mann-Whitney U test. FIG. 7B is a graph that plots events as a function of (Phaseolus vulgaris leukoagglutinin) L-PHA concentration, and shows that GlcNAc treatment increased N-glycan branching in T cells as seen by L-PHA staining in representative mice taken at the peak of disease. The results are representative of at least three mice compared from each group. FIG. 7C shows FACS plots that indicate a significant reduction in CD25⁺T cells was observed in representative GlcNAc-treated mice taken at the peak of disease compared with control mice. The results are representative of at least three mice compared from each group. FIG. 7D shows graphs that plot IFN-γ, TNF-α, IL-17, or IL-22 concentration in CD3⁺T cells isolated from control or GlcNAc treated mice as a function of MOG 35-55 immunization concentration. FIG. 7D shows that in vivo treatment with GlcNAc inhibited production of pro-inflammatory cytokines IFN-γ, TNF-α, IL-17, and IL-22 upon re-stimulation with MOG 35-55 peptide in vitro. p values in FIG. 7D were determined by t test. *, $p<0.05$; *K, $p<0.01$; KKK, $p<0.001$. Error bars in FIGS. 7A and 7D represent the means±S.E. of duplicate or greater values unless otherwise stated.

Example 4

In the experiments on which the graphs of FIG. 8 were based, EAE was induced in 2D2 TCR transgenic mice by immunization with MOG 35-55 peptide emulsified in Complete Freund's adjuvant and pertussis toxin. GlcNAc mice were treated orally with GlcNAc by supplementing their drinking water with GlcNAc at 0.25 mg/ml starting on the second day after disease onset and continued for the duration of the study and control mice were given drinking water supplemented with no GlcNAc (n=10 per control group, n=8 per GlcNAc group). Day 1 indicates the first day of disease onset. Mice were examined daily for clinical signs of EAE over the next 40 days with the observer blinded to treatment conditions and scored daily as follows: 0, no disease; 1, loss of tail tone; 2, hindlimb weakness; 3, hindlimb paralysis; 4, forelimb weakness or paralysis and hindlimb paralysis; 5, moribund or dead. Mice that scored ≤4 were included in the moderate-severe disease group (FIG. 8A), and mice with scores of 5 (i.e., died within the first 40 days after disease onset) (FIG. 8B) were included in the lethal disease group. Mean clinical scores per group daily were compared by the Mann-Whitney U test. FIG. 8C is a graph that plots L-PHA MFI for control and GlcNAc treated mice. The data plotted in FIG. 8C was obtained from experiments in which two representative mice from each group of the 2D2 TCR transgenic EAE experiment were used to assess expression of branched N-glycans. Splenocytes were harvested from the immunized mice and stained with anti-CD4 and L-PHA lectin in triplicate and analyzed by FACS.

Example 5

Figure 9:
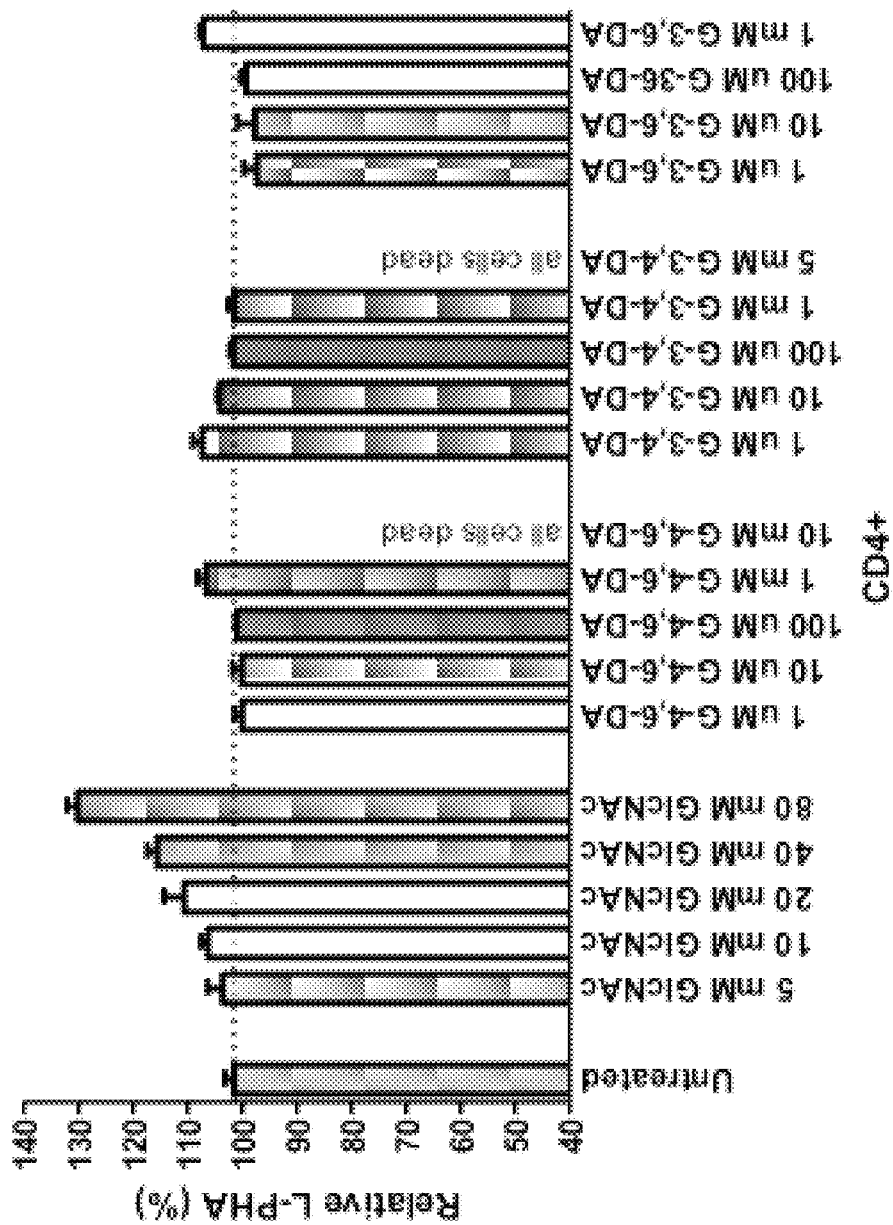
FIG. 9 is a graph illustrating experimental data demonstrating that in human T cells, GlcNAc increases N-glycan branching to greater effect than N-acetylglucosamine-diacetate compounds (i.e., N-acetylglucosamine 3,4 diacetate or N-acetylglucosamine 3,6 diacetate or N-acetylglucosamine 4,6 diacetate). Relative L-PHA (%) in human T cells is plotted as a function of PMA/Ionomycin stimulation and GlcNAc/GlcNAc-diacetate concentrations.

FIG. 9 shows that in human T cells, GlcNAc increases N-glycan branching to greater effect than N-acetylglucosamine-diacetate compounds (i.e., N-acetylglucosamine 3,4 diacetate or N-acetylglucosamine 3,6 diacetate and N-acetylglucosamine 4,6 diacetate).

Example 6

Figure 10:
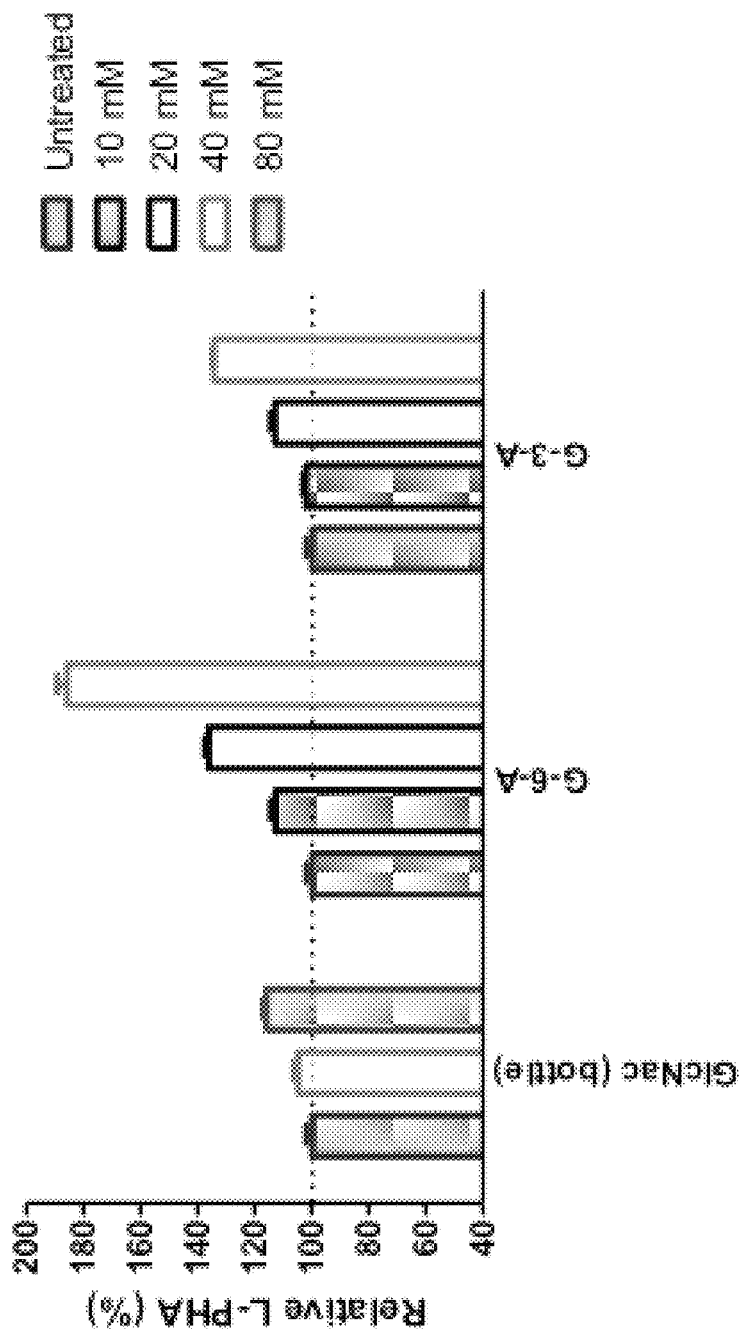
FIG. 10 is a graph illustrating experimental data demonstrating that in human T cells, N-acetylglucosamine 6-acetate increases N-glycan branching to greater effect than GlcNAc or N-acetylglucosamine 3-acetate. Relative L-PHA (%) in human T cells is plotted as a function of PMA/Ionomycin stimulation and GlcNAc/GlcNAc-monoacetate concentrations.

FIG. 10 shows that in human T cells N-acetylglucosamine 6-acetate increases N-glycan branching to greater effect than GlcNAc or N-acetylglucosamine 3-acetate.

Example 7

Figure 11:
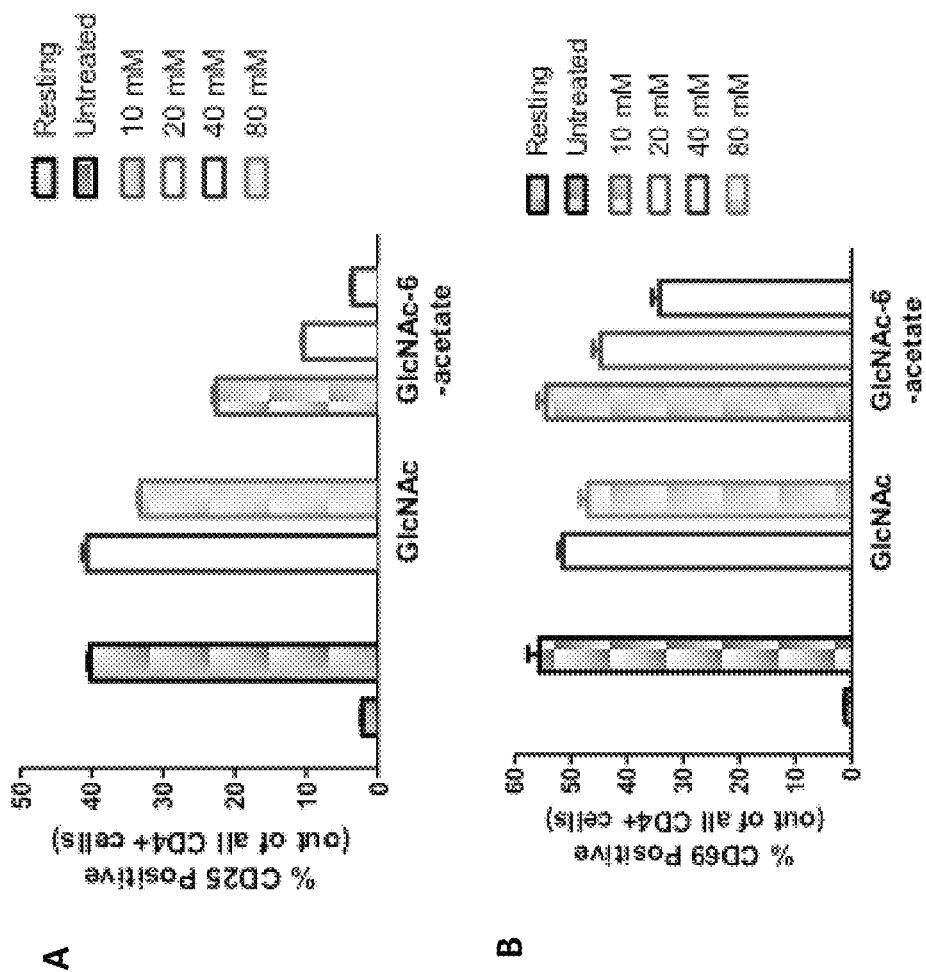
FIG. 11, comprising

FIG. 11 shows that in human T cells, N-acetylglucosamine 6-acetate inhibits CD25 and CD69 expression to greater effect than GlcNAc.

Example 8

Figure 12:
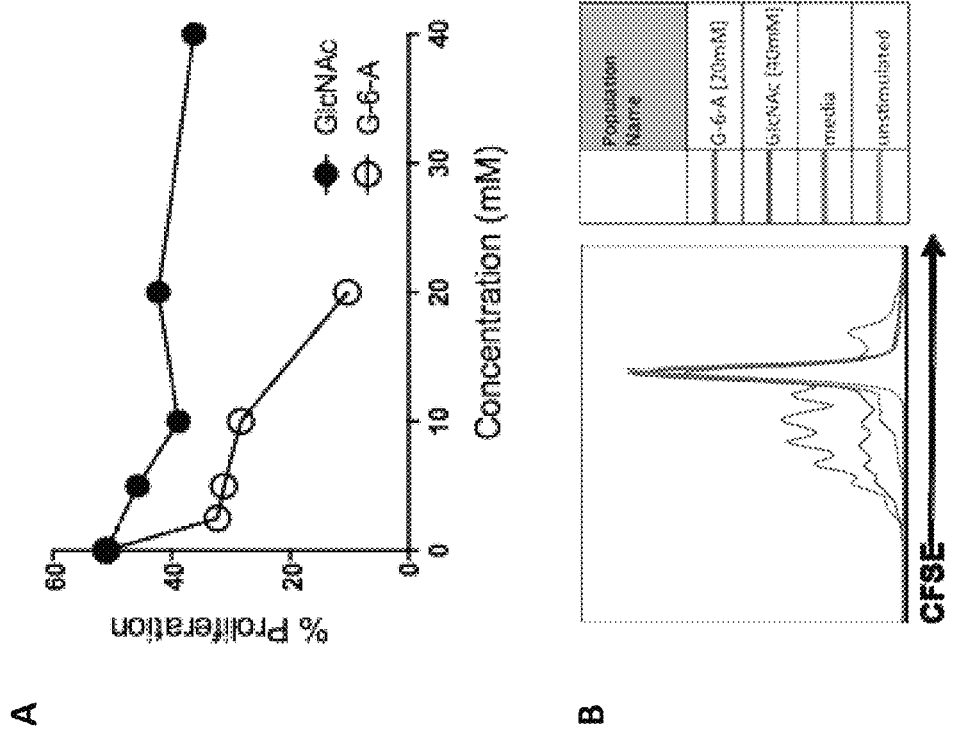
FIG. 12, comprising

FIG. 12 shows experimental data from human CD4$^+$T cells treated with GlcNAc and GlcNAc 6-acetate. Human CD4$^+$T cells were stimulated with anti-CD3 (10 µg/ml) and anti-CD28 (5 µg/ml) and treated as indicated for 5 days. T cell proliferation was measured by CFSE dilution. CD4$^+$T cells were labeled with 1 µM of CFSE prior to in vitro activation for 5 days. Overlaying histograms are gated on live, CD4$^+$ cells by FACS.

Example 9

Figure 13:
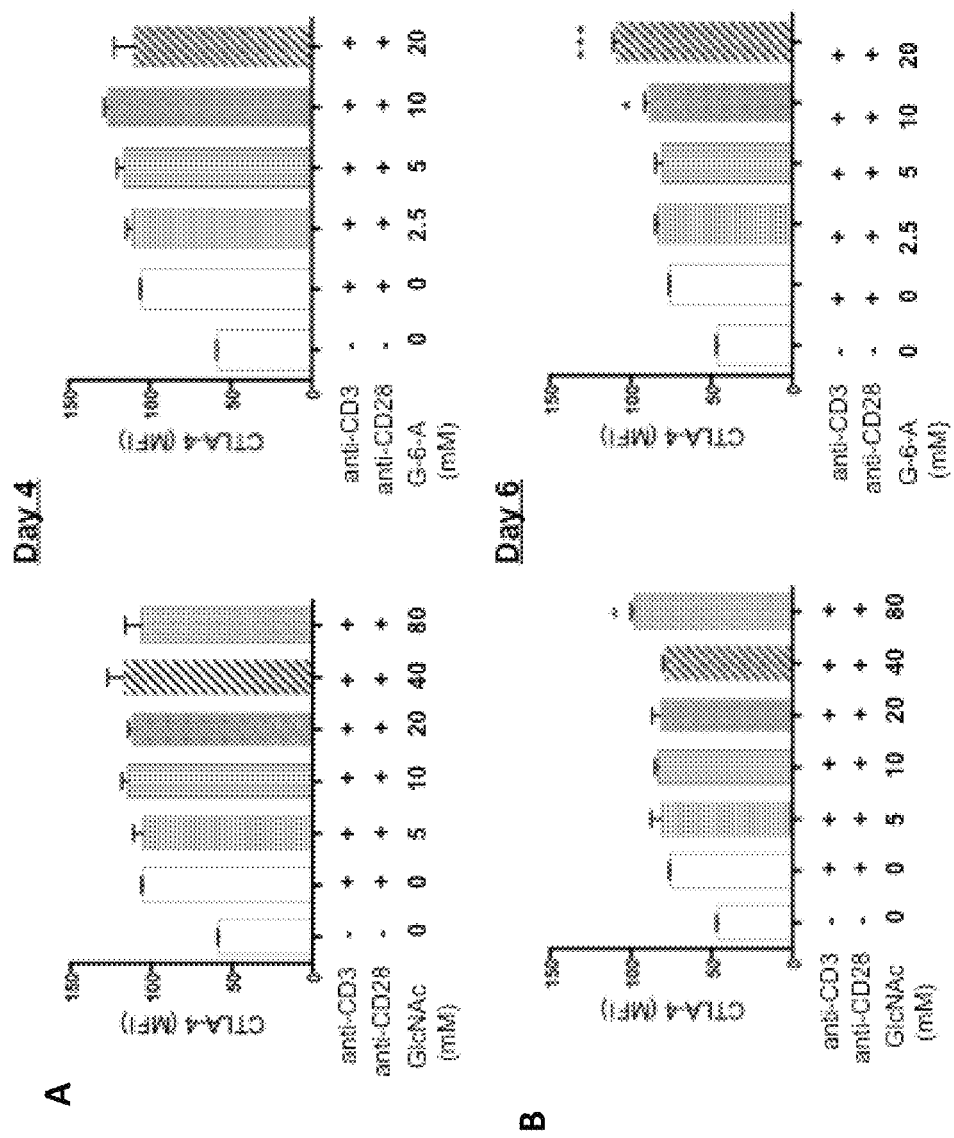
FIG. 13, comprising

FIG. 13 shows experimental data from human CD4$^+$T cells treated with GlcNAc and GlcNAc 6-acetate. Cells were harvested at days 4 and 6 and analyzed for surface CTLA-4 expression (MFI) by FACS. p values were determined by one-way ANOVA-Bonferroni's multiple comparison test. *, p<0.05; , p<0.01; *, p<0.001. Error bars represent the means±S.E.

Example 10

Figure 14:
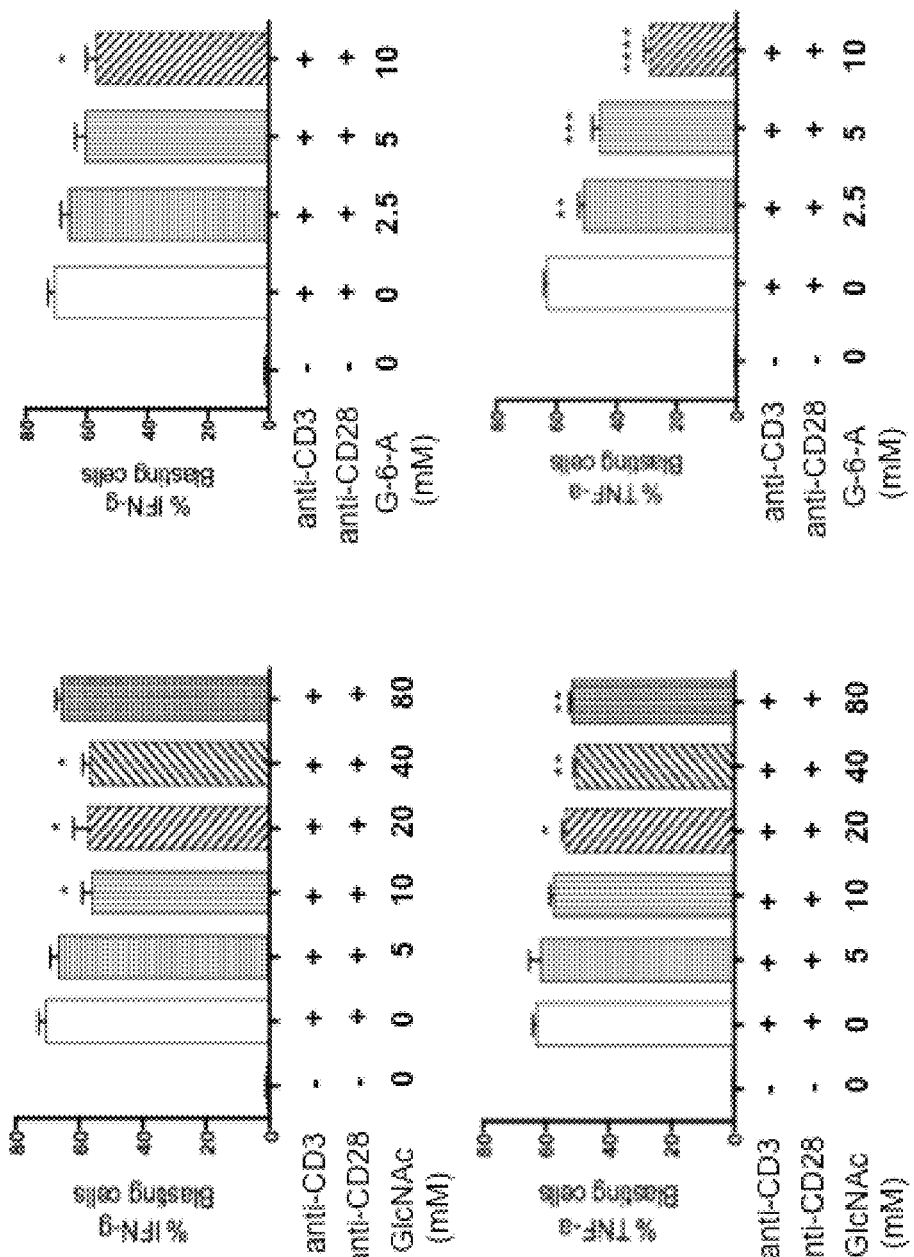
FIG. 14 is a series of graphs illustrating experimental data from human CD4$^+$T cells treated with GlcNAc and GlcNAc 6-acetate. The human CD4$^+$T cells were stimulated with anti-CD3 (10 μg/ml) and anti-CD28 (5 μg/ml) and treated as indicated. Cells were harvested at day 5 and analyzed for IFN-γ and TNF-α expression (%) by FACS. p values were determined by one-way ANOVA-Bonferroni's multiple comparison test. *, $p<0.05$; , $p<0.01$; *, $p<0.001$; ****, $p<0.0001$. Error bars represent the means±S.E.

FIG. 14 shows experimental data from human CD4$^+$T cells treated with GlcNAc and GlcNAc 6-acetate. The human CD4$^+$T cells were stimulated with anti-CD3 (10 µg/ml) and anti-CD28 (5 µg/ml) and treated as indicated. Cells were harvested at day 5 and analyzed for IFN-γ and TNF-α expression (%) by FACS. p values were determined by one-way ANOVA-Bonferroni's multiple comparison test. *, p<0.05; , p<0.01; *, p<0.001; ****, p<0.0001. Error bars represent the means±S.E.

Example 11

Figures 15A, 15B, 15C, 15D:
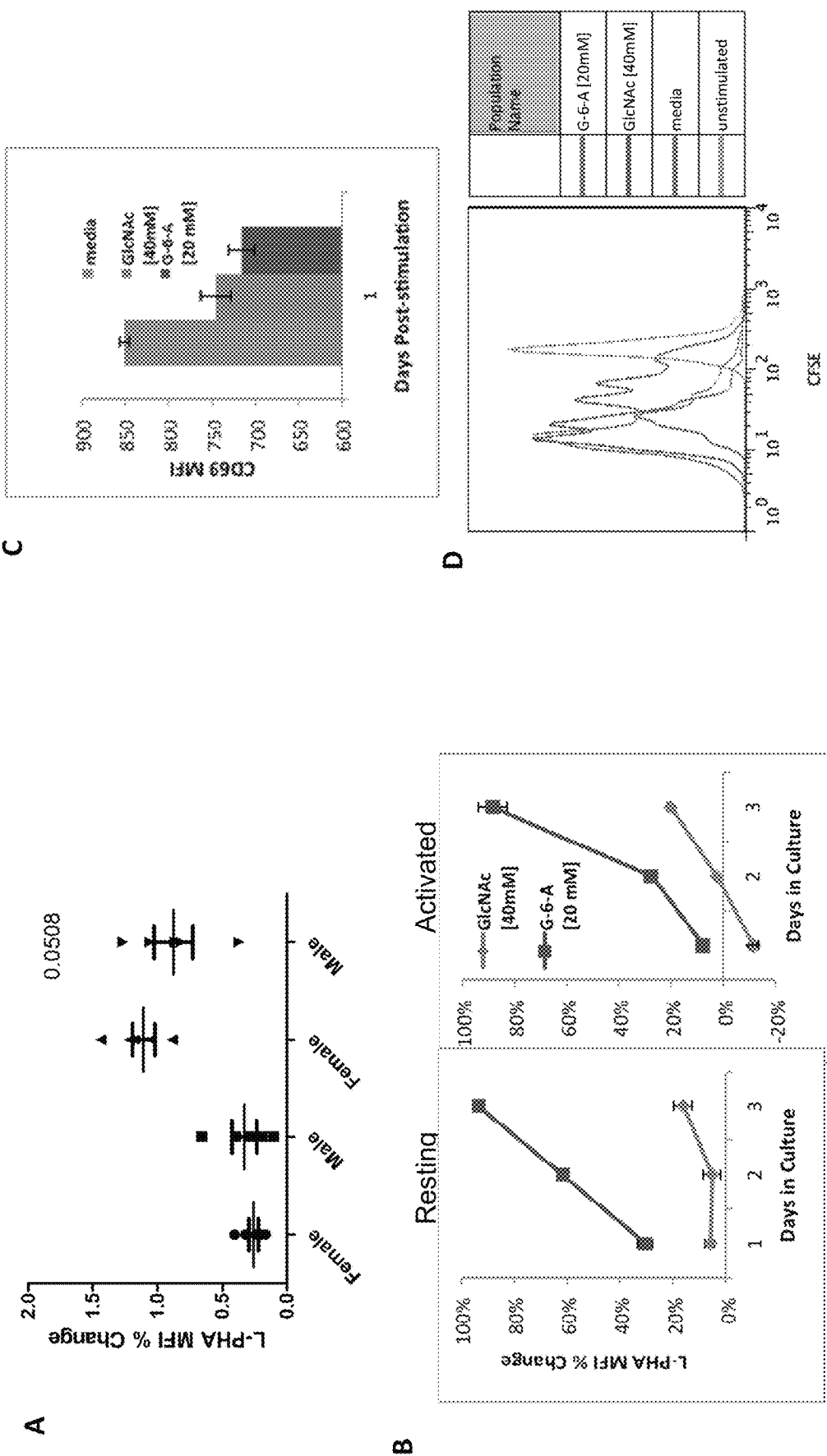
FIGS. 15A-15E, illustrates experimental data demonstrating that N-acetylglucosamine 6-acetate is more effective than GlcNAc in mouse T cells.

FIG. 15A shows splenocytes from C57/BL6 female (n=6, 8-24 weeks old) or male (n=5, 10-13 weeks old) mice after culturing in the presence of anti-CD3 (1 µg/mL). Cells were collected on day 3, and labeled for FACS analysis. Data shown is on gated CD4$^+$ cells, and percent changes of L-PHA MFI were normalized to a media only control.

FIG. 15B shows in vitro cultures of splenocytes either un-stimulated (resting) or anti-CD3 (1 µg/mL) activated. G-6-A (20 mM) and or GlcNAc (40 mM). Cells were harvested over a three-day time course, and labeled for FACS analysis. Data shown is on gated CD4$^+$ cells, and percent changes of L-PHA MFI were normalized to a media only control.

FIG. 15C shows in vitro stimulated splenocytes (anti-CD3 at 1 µg/mL) were cultured for three-days and labeled for FACS analysis of the T cell activation marker CD69 at the time points indicated. Data shown is on gated CD4$^+$ cells.

FIG. 15D shows T cell proliferation as measured by CFSE dilution. Splenocytes were labeled with 1 uM of CFSE prior to in vitro anti-CD3 (1 µg/mL) activation for three-days. Overlaying histograms is on gated CD4+ cells.

Figure 15E:
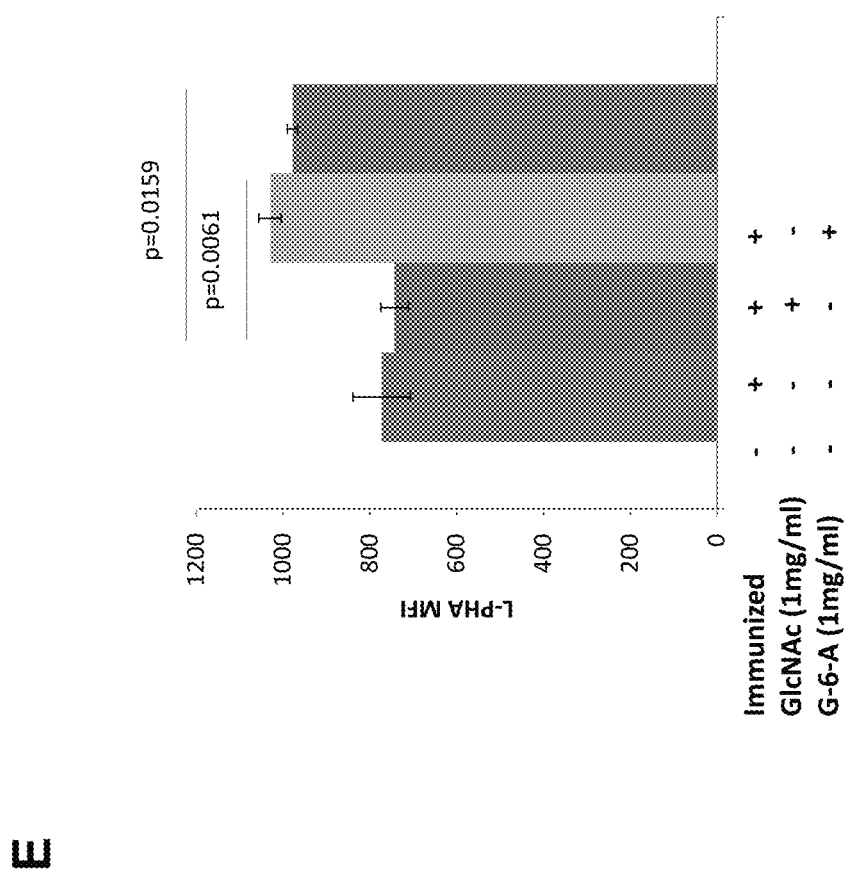

FIG. 15E shows that oral treatment with G-6-A increases N-glycan branching in mouse T cells in vivo. Ten-week old female C57/BL6 were immunized with 100 µg of MOG35-55 peptide in a 1:1 mixture with CFA. Groups were non-immunized (n=2), immunized and given drinking water alone (n=3), immunized and given GlcNAc at 1 mg/mL in drinking water (n=3), or immunized and given G-6-A at 1 mg/mL in drinking water (n=3). Splenocytes were harvested five days post immunization, and labeled for FACS analysis. For GlcNAc and G-6-A treated groups, each mouse drank an average of 3 mL per day. Data shown is gated on a blasting region on CD4$^+$ cells.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a disease or disorder selected from the group consisting of multiple sclerosis (MS), autoimmune diabetes, pediatric treatment-resistant inflammatory bowel disease, psoriasis, psoriatic arthritis, and rheumatoid arthritis (RA) in a subject in need thereof, the method comprising administering to the subject a therapeutically effective amount of a pharmaceutical composition comprising a compound selected from the group consisting of:
    N-acetylglucosamine 6-acetate,
    N acetylglucosamine 3-acetate, a salt or solvate thereof, and any combinations thereof;
    wherein the therapeutically effective amount is sufficient to increase amounts of branched N-glycans in the subject.

2. The method of claim 1, wherein the compound is N-acetylglucosamine 6-acetate, or a salt or solvate thereof.

3. The method of claim 1, wherein the method further comprises administering to the subject at least one additional compound selected from the group consisting of an agonist of complex-branched N-glycans, a sugar donor for complex branched N-glycans, a metabolite of pathways for synthesis of a sugar nucleotide donor or precursors thereof, or a regulator of agonists of a sugar donor or a pathway for the synthesis of a sugar donor, and any combination thereof.

4. The method of claim 1, wherein the method further comprises administering to the subject at least one additional compound selected from the group consisting of an agent used for the treatment of multiple sclerosis (MS), a disease-modifying antirheumatic drug (DMARD), an immunosuppressive agent, an analgesic, an intravenous immunoglobulin (IVIG), an anti-inflammatory agent, and a neutraceutical.

* * * * *